United States Patent
Turcott

(10) Patent No.: US 6,409,675 B1
(45) Date of Patent: Jun. 25, 2002

(54) EXTRAVASCULAR HEMODYNAMIC MONITOR

(75) Inventor: Robert Turcott, Menlo Park, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/438,017

(22) Filed: Nov. 10, 1999

(51) Int. Cl.$^7$ .............................................. A61B 5/04
(52) U.S. Cl. .................. 600/508; 600/504; 600/586; 600/528; 600/526; 600/527
(58) Field of Search ............................. 600/480, 481, 600/486, 504, 586, 489, 508, 526–528

(56) References Cited

U.S. PATENT DOCUMENTS

| | | | |
|---|---|---|---|
| 4,815,469 A | 3/1989 | Cohen et al. ............... | 128/634 |
| 4,915,113 A * | 4/1990 | Holman ...................... | 128/691 |
| 5,040,533 A | 8/1991 | Fearnot .................. | 128/419 PG |
| 5,040,538 A | 8/1991 | Mortazavi .................. | 128/633 |
| 5,113,869 A | 5/1992 | Nappholz et al. ............ | 128/696 |
| 5,342,408 A | 8/1994 | DeCoriolis et al. ........... | 607/32 |
| 5,365,932 A * | 11/1994 | Greenhut ...................... | 128/696 |
| 5,368,040 A | 11/1994 | Carney ....................... | 128/700 |
| 5,404,877 A | 4/1995 | Nolan et al. ................. | 128/671 |
| 5,411,031 A | 5/1995 | Yomtov ...................... | 128/706 |
| 5,454,838 A | 10/1995 | Vallana ....................... | 607/19 |
| 5,496,351 A | 3/1996 | Plicchi et al. ................. | 607/17 |
| 5,511,553 A | 4/1996 | Segalowitz ................. | 128/696 |
| 5,518,001 A | 5/1996 | Snell .......................... | 128/697 |
| 5,544,661 A | 8/1996 | Davis et al. ................. | 128/700 |
| 5,556,421 A | 9/1996 | Prutchi et al. ................ | 607/36 |
| 5,720,770 A | 2/1998 | Nappholz et al. ............. | 607/30 |
| 5,743,268 A | 4/1998 | Kabal ......................... | 128/691 |
| 5,788,643 A | 8/1998 | Feldman ..................... | 600/506 |
| 5,791,344 A | 8/1998 | Schulman et al. .......... | 128/635 |
| 5,792,197 A | 8/1998 | Nappholz ..................... | 607/17 |
| 5,836,889 A | 11/1998 | Wyborny et al. ............ | 600/509 |
| 5,904,708 A | 5/1999 | Goedeke ....................... | 607/18 |
| 5,935,081 A | 8/1999 | Kadhiresan ................. | 600/513 |
| 6,045,513 A * | 4/2000 | Stone et al. ................. | 600/508 |
| 6,077,227 A * | 6/2000 | Miesel et al. ............... | 600/486 |
| 6,264,611 B1 * | 7/2001 | Ishikawa et al. ............ | 600/486 |
| 6,312,378 B1 | 11/2001 | Bardy ......................... | 600/300 |

OTHER PUBLICATIONS

Medtronic Investor Information; Press Release "Medtronic Announces Two Major Milestones in its Effort to Treat Patients with Heart Failure"; Jun. 16, 1999; pp. 1–3.
Medtronic Reveal—A New Tool—Sycope and Fainting; New Diagnostic Tool; Jun. 16, 1999; pp. 1–3.

* cited by examiner

*Primary Examiner*—Carl Layno
(74) *Attorney, Agent, or Firm*—Steven M. Mitchell

(57) ABSTRACT

A method and apparatus for monitoring the hemodynamic status of a patient is provided. It comprises an implantable monitor with one or a plurality of sensors configured for extravascular placement, electronic circuitry that is coupled to the sensors and processes their output, a transmitter/receiver for conveying information between the monitor and an external unit, and a patient alert which notifies the patient if medical attention should be sought. The extravascular sensors include vascular plethysmography, heart and lung sounds, thoracic impedance, and ECG. In the preferred embodiment, the radio frequency transmitter/receiver provides for the automatic telemetry of data, without requiring the active participation of the patient or clinician. Thus data can be conveyed routinely and automatically, allowing more computationally demanding analysis to be done by an external device, or allowing human review at a central location. The monitor is particularly applicable to patients with heart failure.

27 Claims, 21 Drawing Sheets

EXTRAVASCULAR HEMODYNAMIC MONITOR

BACKGROUND OF THE INVENTION

I. Field of the Invention

This invention relates generally to implantable monitoring devices, and more particularly to monitoring the hemodynamic status of a patient with a chronic disease such as heart failure, ischemic heart disease, or diabetes.

II. Description of the Related Art

Many chronic diseases, such as diabetes and heart failure, require close medical management to reduce morbidity and mortality. Because the disease status evolves with time, frequent physician follow-up examinations are often necessary. At follow-up, the physician may make adjustments to the drug regimen in order to optimize therapy. This conventional approach of periodic follow-up is unsatisfactory for some diseases, such as heart failure, in which acute, life-threatening exacerbations can develop between physician follow-up examinations. It is well know among clinicians that if a developing exacerbation is recognized early, it can be easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease.

It is often difficult for patients to subjectively recognize a developing exacerbation, despite the presence of numerous physical signs that would allow a physician to readily detect it. This problem is well illustrated by G. Guyatt in his article entitled "A 75-Year-Old Man with Congestive Heart Failure," 1999, *JAMA* 281(24)2321–2328. Furthermore, since exacerbations typically develop over hours to days, even frequently scheduled routine follow-up with a physician cannot effectively detect most developing exacerbations. It is therefore desirable to have a system that allows the routine, frequent monitoring of patients so that an exacerbation can be recognized early in its course. With the patient and/or physician thus notified by the monitoring system of the need for medical intervention, a developing exacerbation can easily and inexpensively be terminated early in its course.

The multiplicity of feedback mechanisms that influence cardiac performance places the heart at the center of a complex control network. The neurohumoral axis includes the autonomic nervous system, consisting of sympathetic and parasympathetic branches, and numerous circulating hormones such as catacholamines, angiotensin, and aldosterone. Neural reflex arcs originating from pressure and stretch receptors, which directly measure mechanical hemodynamic status, modulate the neurohumoral axis. Similarly, chemoreceptors respond to changes in $CO_2$, pH, and $O_2$, which assesses cardiopulmonary function. The neurohumoral system influences cardiac performance at the level of the cardiac electrical system by regulating heart rate and the conduction velocity of electrical depolarizations. It also influences cardiac performance at the mechanical level, by controlling contractility, that is, the effective vigor with which the heart muscle contracts. Conventional cardiac monitors, such as defibrillators, pacemakers, Holter monitors, and cardiac event records, are tailored for the diagnosis and/or therapy of abnormalities of the cardiac electrical system. In contrast, heart failure is a disease of the cardiac mechanical system: it is primarily a failure of the myocardium to meet the mechanical pumping demands required of it. In monitoring the status of a heart failure patient, measuring the mechanical hemodynamic variables is clearly desirable. Examples of mechanical hemodynamic variables include atrial, ventricular, and arterial pressures, and cardiac output (volume of blood pumped into the aorta per unit time). However, because of the complex feedback network that monitors and controls cardiac performance, measuring variables that do not directly reflect the mechanical performance of the heart is also useful. In this way, measuring cardiac electrical activity to assess heart rate variability (described below) allows one to infer the state of the autonomic nervous system, which allows one to infer information about the hemodynamic status of a heart failure patient. Similarly, recognition of Cheyney-Stokes respiration (described below) via respiratory pattern analysis, hemoglobin saturation analysis, and blood gas analysis allows one to detect the presence of pulmonary edema, and thereby detect an acute heart failure exacerbation, though none of these parameters directly measure mechanical hemodynamic status.

One approach to frequent monitoring of heart failure patients that has been proposed is the daily acquisition of the patient's weight and responses to questions about subjective condition (Alere DayLink Monitor, Alere Medical, Inc., San Francisco, Calif.). The simplicity and noninvasive embodiment of this approach are desirable features. However, both the amount and the sophistication of the objective physiological data that can be acquired in this way are quite limited, which consequently limits the accuracy of the system. Furthermore, the system requires the active participation of the patient, who must not deviate from the precise data acquisition routine or risk introducing confounding factors into the acquired data.

Some of these limitations have been addressed by the development of an implantable system that monitors hemodynamic status (Medtronic Chronicle, Medtronic, Inc., Minneapolis, Minn.). While this system potentially avoids the need for active patient participation, it relies on an intravascular sensor placed in the right ventricle of the heart. This approach is consistent with the prior art for implantable hemodynamic status monitoring, which has to date focused on intravascular or intramyocardial instrumentation. Examples include U.S. Pat. No. 5,454,838 in which Vallana et al. teach placement of a sensor on the myocardial wall using an intravascular approach. In U.S. Pat. No. 5,496,351, Plicchi et al. propose placing a sensor within the myocardial wall. Mortazavi in U.S. Pat. No. 5,040,538 and Cohen et al. in U.S. Pat. No. 4,815,469 describe placement of an optical sensor within the right ventricle. In the context of hemodynamic assessment for arrhythmia discrimination, Cohen and Liem (*Circ.*, 1990, 82:394–406) study the effectiveness of a pressure transducer placed in the right ventricle. Clearly, powerful information about hemodynamic status can be obtained using intravascular instrumentation. However, intravascular or intramyocardial instrumentation carries significant risks to the patient, including increased perioperative morbidity and mortality, and increased long-term risks such as stroke and pulmonary embolism. Furthermore, intravascular instrumentation can only be performed by extensively trained specialists, thereby limiting the availability of qualified physicians capable of implanting the device, and increasing the cost of the procedure. Finally, because of the added patient risks and greater physical demands of an intravascular environment, the intravascular placement of the sensor increases the cost of development, manufacturing, clinical trials, and regulatory approval.

Though not directly related to hemodynarnic status monitoring, extravascular sensing of cardiac electrical activity is known in the art. Early generations of implantable pacemakers and defibrillators relied on epicardial placement of sensing electrodes. Epicardial electrodes still see use in special patient populations. Extrathoracic sensing of cardiac electrical activity is also possible, which avoids the need for direct contact with the heart, and thus decreases the difficulty of the implant procedure and reduces the risk of perioperative complications. An example of this approach is the Reveal Insertable Loop Recorder (Medtronic, Inc., Minneapolis, Minn.), a cardiac event recorder configured for short-term implantation. As a temporarily implantable recorder, it overcomes some of the technical difficulties associated with conventional externally worn recorders of cardiac electrical activity. Two general types of externally worn recorders are Holter monitor recorders, which record continuously for an extended period of time, and cardiac event recorders, such as the King of Hearts (Alaris Medical Systems, San Diego, Calif.), which use a loop memory to retain the most recent history of cardiac electrical activity. Both these approaches require surface contact electrodes which are cumbersome and inconvenient for the patient, and more susceptible to motion artifact than an implanted electrode. However, like conventional cardiac event recorders and continuous Holter monitor recorders, the Reveal Insertable Loop Recorder is designed for short-term use as a diagnostic aid. More importantly, it requires active patient participation; when the patient recovers from a syncope, or becomes aware of symptoms, he must signal to the event recorder by means of an Activator that the recent data should be retained in long-term memory for later review by a physician. After diagnosis the Reveal Insertable Loop Recorder is explanted from the patient. Thus the Reveal is intended for short-term recording for diagnostic use, is limited to recording the electrical activity of the heart, and does not attempt to measure or quantify the hemodynamic status of the patient beyond screening for cardiac arrhythmias.

An extension of the short-term recorders just described is the Implantable Ambulatory Electrocardiogram Monitor described by Nappholz et al in U.S. Pat. No. 5,113,869, incorporated herein by reference. This device is designed for chronic extravascular implantation. In contrast to cardiac recorders, it performs analysis on the electrocardiogram signal in order to predict imminent cardiac arrhythmias and to detect cardiac ischemia. Like the cardiac recorders, it is capable of storing raw ECG data for later review by a physician. This feature, along with the record of arrhythmic events it detected, allows the physician to tailor pharmacologic therapy. In addition, Nappholz et al. mention the use of transthoracic impedance for minute ventilation, ultrasound transducers for arterial pressure, or other sensors to allow discrimination of arrhythmias from normal cardiac rhythms caused by exertion or physiologic stress.

While the Holter monitor recorder, the Reveal Insertable Loop Recorder, and the Implantable Ambulatory Electrocardiogram Monitor provide important clinical utility in recording and monitoring cardiac electrical activity, none is designed to monitor hemodynamic status. Indeed, cardiac electrical activity does not, by itself, provide unambiguous information about hemodynamic status. By sensing only cardiac electrical activity, they are unable to distinguish between, for example, a hemodynamically stable cardiac rhythm and Pulseless Electrical Activity (PEA), a condition in which the heart is depolarizing normally, and thus generating a normal electrical pattern, but is not pumping blood. Furthermore, these devices are unable to recognize or quantify subtle changes in the patient's hemodynamic status. What is needed is an extravascular, hemodynamic monitor designed for chronic use.

While much of the prior art has focused on intravascular instrumentation, as discussed above, some proposal has been made to incorporate physiologic sensors into the implantable cardiac device itself. Fearnot in U.S. Pat. No. 5,040,533 teaches placement of a generalized window in the housing of the cardiac device. The window might be transparent to facilitate the transmission of light or flexible to facilitate pressure transduction. While the convenience, from the clinician's perspective, of incorporating the sensors into the housing of the cardiac device is an obvious advantage, the technical difficulty in maintaining a hermetic seal between two different materials, particularly in a chronically implanted device, is equally obvious to one skilled in the art. The technical in challenge is made more difficult by the greatly increased circumference, relative to that of standard feed-through connections known in the art, of the boundary between the window and the device housing. What is needed, therefore, is a method of placing a hemodynamic sensor in or on the device without compromising the integrity of the hermetic enclosure.

Prutchi et al., in U.S. Pat. No. 5,556,421 propose placement of a sensor within the header of a cardiac device. While this is an obvious solution for devices that have external leads requiring headers, it presupposes the existence of a header, and therefore does not address the implantable device that lacks a header. Furthermore, while appending a header to one end or pole of an implantable device is an efficient solution when external leads are required, appending a header-like sensor unit to one end or pole of a device not otherwise requiring a header, where the sensor unit is itself, like a header, the full-thickness of the device, is an inefficient use of volume. Thus, the approach of Prutchi et al. used in a device that doesn't otherwise require a header would be to append a header or a header-like sensor unit to one end or pole of the device, but this would unnecessarily increase both the volume and the expense of the device. A further disadvantage of placing a sensor in a header is that it does not necessarily provide for the optimal signal transduction of a particular sensor. For example, the performance of the optical sensor described in the above referenced U.S. Pat. No. 5,556,421 would be so severely degraded by direct transmission of light from source to detector that one skilled in the art would question the functionality of the proposed solution. In addition, placement in a rigid epoxy header is simply not an option for some sensors, such as sound sensors, because of the dramatic degradation in the signal-to-noise ratio the rigid header would impose. What is needed is a method of incorporating a hemodynamic sensor into a implantable device, providing it optimal access to the external milieu so that the signal of interest is optimally transduced, maintaining the hermetic enclosure provided by the device housing, and minimizing the added volume that the sensor imposes.

A solution to this challenge is offered in U.S. Pat. No. 5,404,877 by Nolan et al, in which an arrhythmia detection and warning system is described. The monitor avoids external leads and sensors by generating a radio frequency electromagnetic field within the device, which is intended to propagate through the device housing, reflect off internal organs and structures, and be detected again inside the device housing. The device uses observed changes in impedance seen at the antenna to deduce organ motion, in particular heart motion. While the leadless embodiment is desirable for the reasons described by Nolan et al., the technical challenges associated with inferring useful physiologic information from changes in impedance is obvious to one skilled in the art. The general problem is that the large number of confounding factors, e.g., changes in body position, would certainly swamp the subtle impedance changes that might result from changes in cardiac volume with contraction.

Another aspect of the prior art that has been limited is in the communication of information between a device and the clinician. During periodic follow-up in the physician's office, conventional implanted devices such as pacemakers and defibrillators are electronically interrogated and stored data is conveyed outside the body using telemetry. Depending on the physician's assessment, programmable device parameters or the patient's medical regimen may be modified. The process is initiated by the clinician and requires the placement of an external telemetry antenna in close proximity to the implanted device. Indeed, in U.S. Pat. No. 5,342,408 DeCoriolis et al. provide a telemetry signal strength indicator that facilitates the positioning of the external antenna by the clinician. While the prior art is sufficient for conventional cardiac devices, which typically only require telemetry during relatively infrequent follow-up visits, in cases where frequent telemetry is required it is desirable to have a system that does not rely on active human participation. With the Alere system described above, data is conveyed daily over telephone channels to a central location for review, a process that is initiated by the patient and requires interaction of the patient with the device. While in this case the clinician is not actively involved in the telemetry process, the patient is. This approach therefore also precludes a fully automated system. What is needed is a system that provides telemetry at a distance, so that data can be transferred remotely without the active participation of a clinician or cooperation of the patient. With telemetry at a distance, data could be automatically transferred for review and analysis by a clinician or central monitor, and programming parameters of the device could be modified remotely. By not relying on the routine participation of patient or physician, such a system would be more convenient and reliable, would avoid the inconvenience and expense of in-person follow up, and would allow frequent monitoring and tailoring of device parameters and medical therapy as the patient's disease status changes.

In U.S. Pat. No. 5,113,869 to Nappholz et al., telemetry is provided to warn the patient or physician of an impending arrhythmia event. U.S. Pat. No. 5,544,661 to Davis et al. discloses an ambulatory patient monitor that is worn by the patient and provides arrhythmia analysis and wireless two-way data and voice communication to a central station. In the event of an arrhythmia, a clinician can actively and remotely monitor the patient. However, this system is intended for short term use to monitor patients who may be subject to sudden life threatening arrhythmic events. Nappholz et al. in U.S. Pat. No. 5,720,770 discloses a system including an implanted cardiac therapy device and an external portable device in constant or periodic telemetric communication with the implanted device. The external device receives updates of the condition of the patient and the operation of the cardiac therapy device. This information is transmitted by the external device over wireless or wired phone lines to a central monitoring station.

One of the challenges of providing telemetry at a distance is to provide for the efficient transmission and reception of energy by the implanted device. The current art places the telemetry coil inside the implantable cardiac device housing and uses magnetic inductive coupling to convey data between the implanted and external units. The metallic housing attenuates the magnetic field, but since the clinician is available to actively position the external coil the degree of attenuation is tolerable. The above referenced U.S. Pat. No. 5,404,877 describes radio-frequency electromagnetic telemetry, rather than the conventional magnetic-induction method commonly used in pacemakers and implantable defibrillators. However, like the conventional magnetic coil, the RF antenna is placed within the device housing, which has the undesirable effect of attenuating the signal strength. The above referenced U.S. Pat. No. 5,113,869 discloses a radio frequency telemetry system similar to that described in above referenced U.S. Pat. No. 5,404,877, but with the antenna placed outside the device housing on a lead that extends away from the device. The configuration is desirable in that attenuation by the metallic housing of the device is avoided, however, it requires subcutaneous tunneling for placement, which causes tissue trauma and increases the risk, both acute and chronic, of infection. Furthermore, patient motion will alter the impedance between the antenna and ground plane, which degrades antenna gain. The above referenced U.S. Pat. No. 5,342,408 teaches placement of an antenna in the device header, which has the advantage of avoiding the attenuation of the metallic housing, as well as avoiding the disadvantages of an antenna that extends away from the device in a lead. However, placement in the header presupposes the existence of external leads requiring a header, which are not necessarily present in a device that uses extravascular sensors. It is desirable, therefore, to provide placement of the telemetry antenna outside the housing of a device which lacks a header. The placement should be such that the antenna is mechanically stabilized and electrically insulated from the device housing and the surrounding tissue.

Because of the considerations described above, the principal object of the present invention is to provide an extravascular device that monitors a patient's hemodynamic status.

An additional goal of the present invention is to provide telemetry at a distance, thereby avoiding the need for active human participation in the data-transfer process.

Another object of the invention is to monitor the status of a chronic disease in order to optimize medical therapy.

A further object is to monitor the status of a chronic disease in order to recognize and facilitate the early termination of a developing exacerbation.

An additional object of the invention is to provide an implantable device, which avoids the need for active patient participation in data acquisition, thereby minimizing the risk of confounding factors.

Yet another object is to provide an implantable device, which allows one or a plurality of sophisticated physiologic measurements to be acquired and processed, thereby improving the accuracy of the assessment of the disease status.

Still another object of the invention is to provide for extravascular placement of the device and sensors, which minimizes the perioperative and long-term risk of complications.

A further object is to provide for extravascular placement of the device and sensors, which requires less training of the physician performing the implant procedure, making the procedure more readily available and less expensive.

An additional object of the invention is to provide for extravascular placement of the device and sensors, which reduces the development, manufacturing, and regulatory costs of the system.

Further objects and advantages will become apparent from a consideration of the ensuing description and drawings

BRIEF SUMMARY OF THE INVENTION

The preferred embodiment of the present invention provides a method and apparatus for monitoring the hemodynamic status of a patient. It comprises an implantable device with one or a plurality of sensors configured for extravascular placement, electronic circuitry that is coupled to the sensors and processes their output, a transmitter/receiver for telemetrically conveying information between the monitor and an external unit, and a patient alert which notifies the patient if medical attention should be sought. In the preferred embodiment, the radio frequency transmitter/receiver provides for the automatic telemetry of data, without requiring the active participation of the patient or clinician. Thus data can be conveyed routinely and automatically, allowing more computationally demanding analysis to be done by an external device, or allowing human review at a central location.

In another embodiment the monitor is not implanted but rather is attached or worn externally by the patient daily for extended periods, such as during sleep.

In a further embodiment, electrodes allow an ECG signal to be acquired and analyzed. Optical sensors determine the arterial blood oxygen saturation and arteriolar volume. A sound sensor records heart and lung sounds. An electrochemical sensor determines the partial pressure of oxygen at the tissue/monitor interface. The ECG signal is used to assess heart rate, and provides the basis of heart rate variability analysis, which reflects the balance of the autonomic nervous system. The vascular volume is also analyzed to assess the autonomic balance. Heart sounds are examined for changes in amplitude and the emergence of extra sounds, which indicate declining hemodynamic status. Lung sounds are analyzed for the presence of pulmonary rates, which is a hallmark of pulmonary edema associated with hemodynamic decline. Finally, the presence of the Cheyne-Stokes respiratory pattern, another sign of failing hemodynamic status, is assessed using heart rate variability derived from the ECG sensor, changes in pulse amplitude derived from the vascular volume sensor, and changes in oxygen saturation and partial pressure derived from the oxygen sensors.

In the preferred embodiment sensors are either integrated into the monitor housing, as is the case for the sound sensor, or are placed outside the monitor housing, mechanically stabilized and electrically isolated with an epoxy encasement, and connected to the electronic circuit within the monitor housing via feed-through connectors, as is the case for optical and electrical sensors. In the preferred embodiment telemetry at a distance is facilitated by an antenna similarly placed and secured outside the monitor housing.

DETAILED DESCRIPTION OF THE INVENTION

Figure 1:
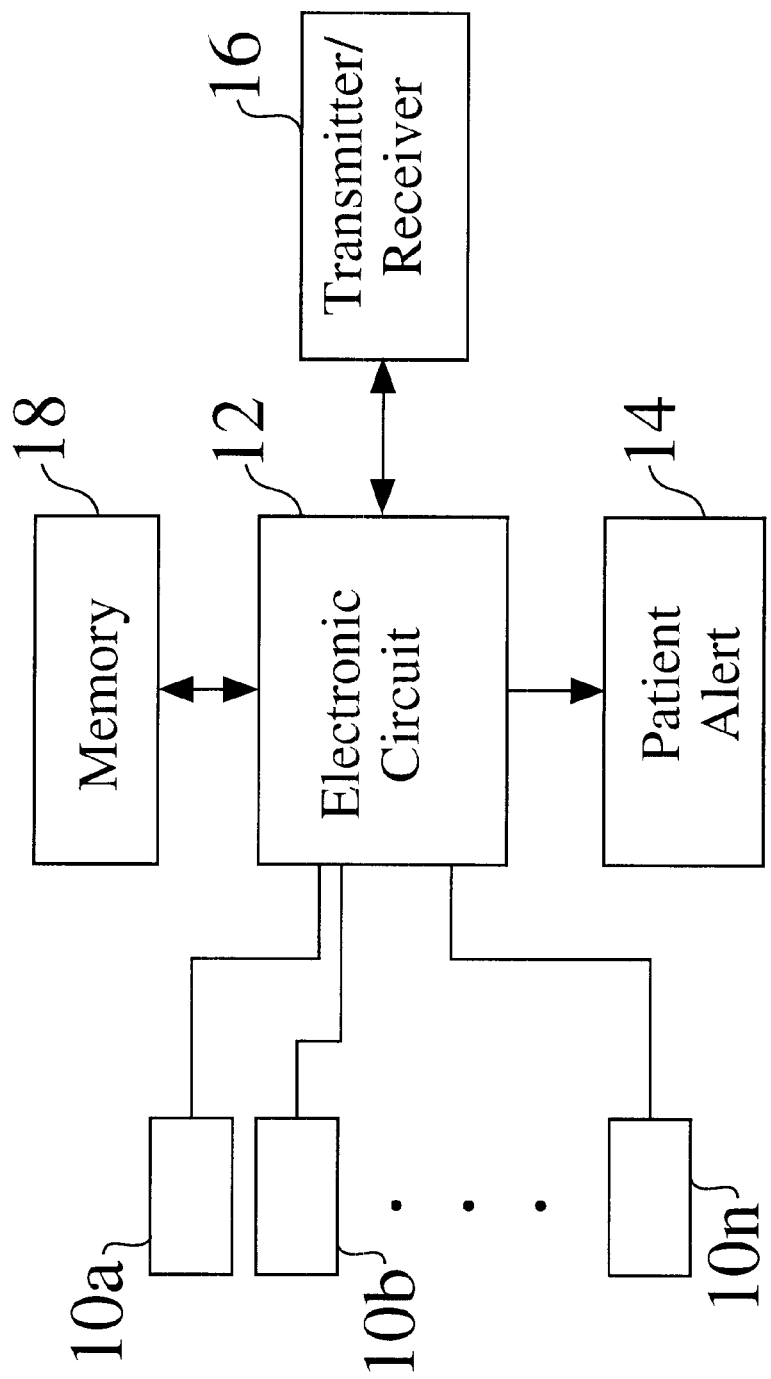
FIG. 1 shows a functional block diagram of a preferred embodiment of the invention.

A functional block diagram of a monitor according to the invention is shown in FIG. 1. One or a plurality of sensors 10a, 10b, . . . 10n is connected to an electronic circuit 12, which in turn is connected to a patient alert 14, transmitter/receiver 16, and memory 18, with each of elements 14, 16 and 18 being optional. In the preferred embodiment, the electronic circuit 12 includes a low-power microprocessor. In alternate embodiments the microprocessor is excluded, or control and higher level processing is performed by a microcontroller, an embedded system, a programmable logic device such as a field-programmable logic array, or a combinatorial implementation of a state machine. In the preferred embodiment the transmitter/receiver 16 is an integrated radio frequency telemetry unit. Other embodiments of the transmitter/receiver are possible, including acoustic, optic, electrostatic, and magnetic. In yet another embodiment the receiver is simply a reed switch capable of sensing the presence of a strong magnet, so that the device can be turned on and off externally, but lacks post-manufacturing programmability. In still other embodiments the patient alert and transmitter/receiver might not be included, so that the device lacks the ability to receive or transmit information. Such a device, by design, may be intended not to be capable of downloading data it has acquired or informing the patient of a change in status. Rather, it may be intended to be explanted in order for the stored data to be accessed. In another embodiment, the monitor lacks a receiver and is intended to run continuously in the same mode from the time of implant, i.e., it lacks programmability.

The patient alert provides notification to the patient. A variety of embodiments are possible, including acoustic, mechanical vibration, optic, thermal, and electrical stimulation. In the preferred embodiment the patient alert is an inductive coil and magnetic which generates both sound and mechanical vibration. In an alternative embodiment, the patient alert function is incorporated into the electronic circuit 12 and transmitter/receiver 16.

Figure 2A:
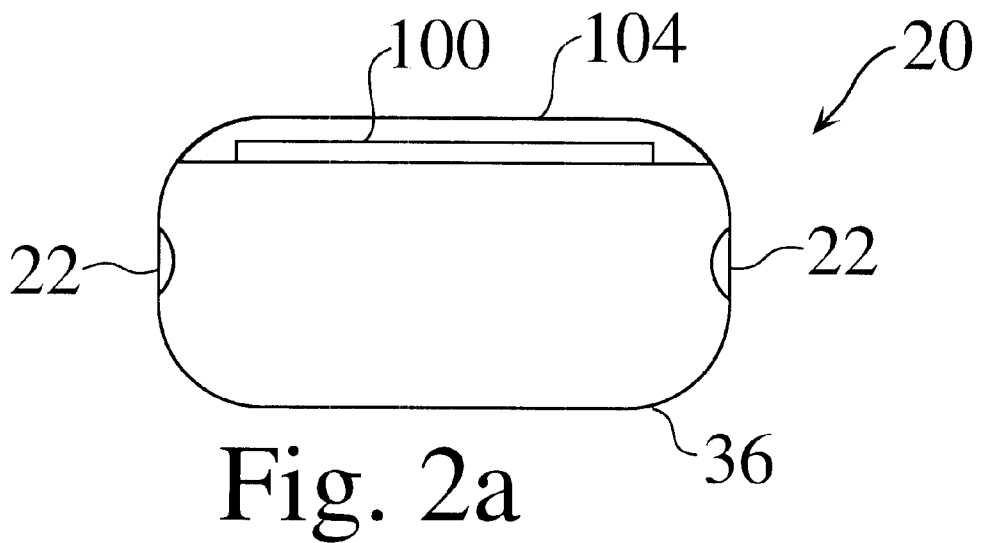
FIGS. 2a–2c provide various views of a preferred embodiment of the invention.
Figure 2B:
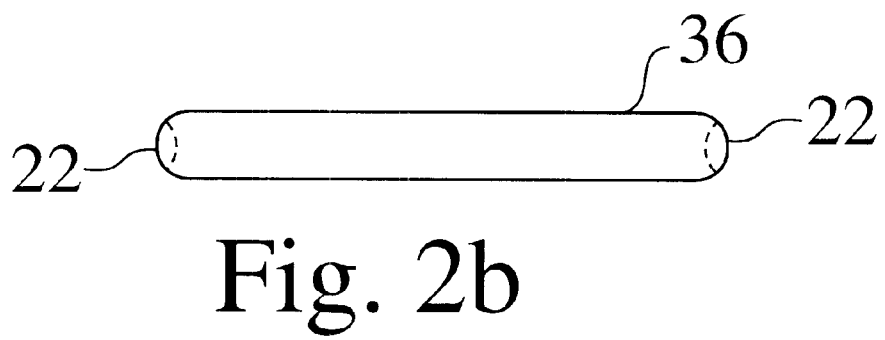
Figure 2C:
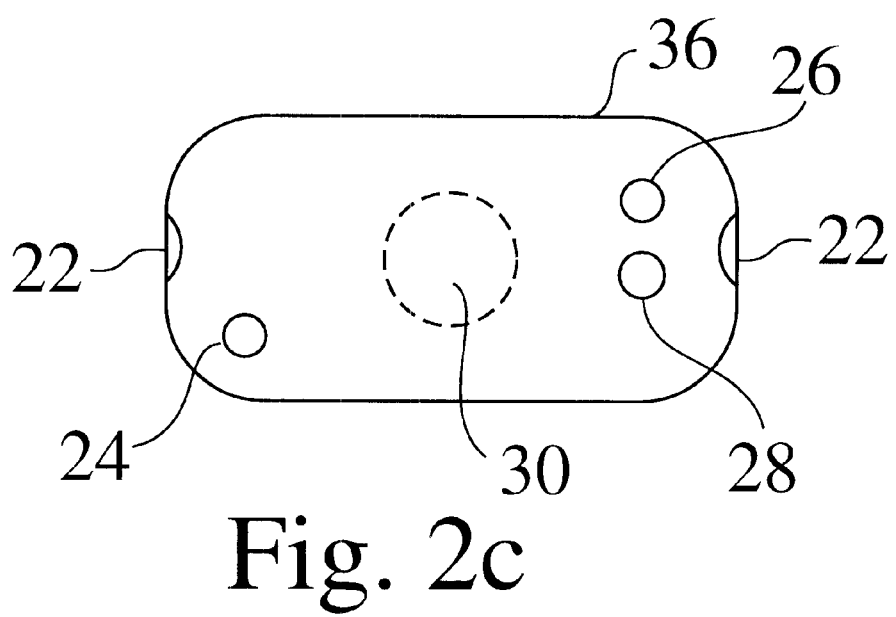
Figure 3A:
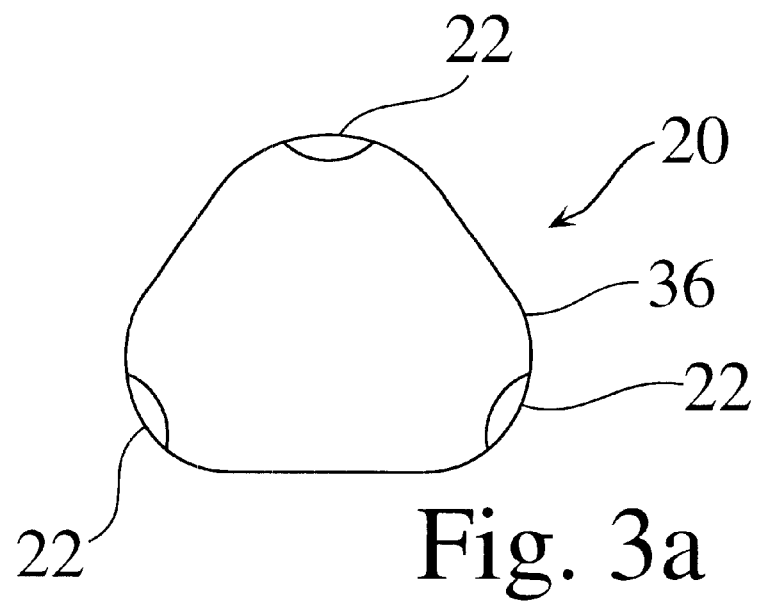
FIGS. 3a–3c provide various views of an alternate embodiment of the invention.
Figure 3B:
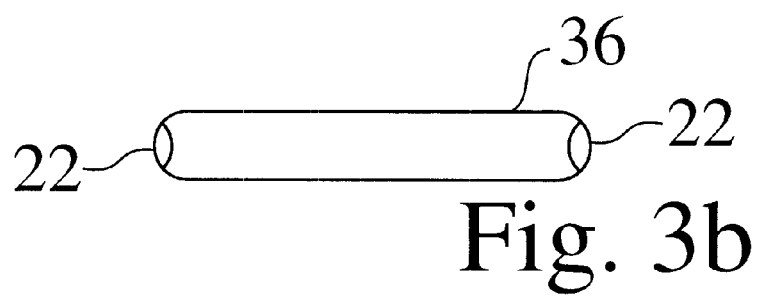
Figure 3C:
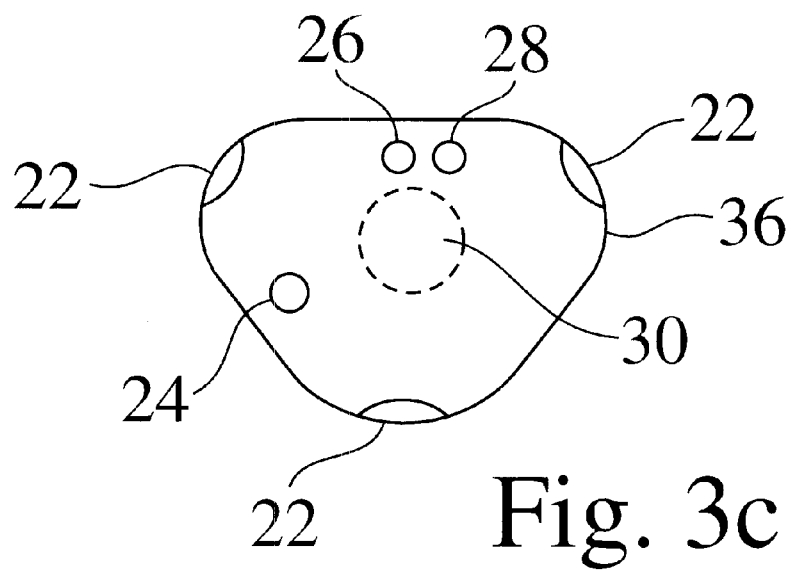

An external view of the monitor 20 is illustrated in FIGS. 2 and 3. In the preferred embodiment shown in FIGS. 2a–2c, the device is small, thin, and oblong, with smooth surfaces and a physiologic contour which minimizes tissue trauma and inflammation. The oblong geometry of the monitor housing 36 is desirable because it maximizes separation of electrodes 22 and prevents rotation of the monitor within the tissue pocket, thereby allowing interpretation of the QRS morphology in an ECG sensed using electrodes 22. An antenna 100, mechanically stabilized and electrically insulated by an epoxy encasement 104, facilitates radio frequency telemetry. Two ECG electrodes 22 are present in the preferred embodiment, one at each end of the oval formed by the monitor housing 36. In the alternate embodiment illustrated in FIGS. 3a–3c, three ECG electrodes 22 are present, one at each apex of the triangle formed by the device housing 36. These three electrodes allow the three standard surface ECG leads I–III to be approximated. In another embodiment, four or more ECG electrodes might be used, with each orthogonal electrode pair providing orthogonal ECG signals. Alternatively, an embodiment lacking ECG electrodes is possible. A further alternative has a single ECG electrode with the monitor housing acting as the other electrode in the pair. In addition to the ECG electrodes, a working electrode 24 of an electrochemical sensor is also shown in FIGS. 2 and 3, such as that previously described in the art in U.S. Pat. No. 4,853,091, which is incorporated herein by reference. In the preferred embodiment this is specific for $O_2$ partial pressure, but other embodiments measure the concentrations or partial pressures of other metabolic gases or products, such as $CO_2$, pH, and lactic acid.

A light source 26 and detector 28, preferably LEDs and photodiode, respectively, are shown in FIG. 2c and FIG. 3c. In the preferred embodiment a single source and a single detector are used for both vascular plethysmography and for measuring the oxygen saturation of arterial hemoglobin. The source is capable of independently generating two discrete wavelengths of light, preferably at 660 and 940 nm, in a way well known to those skilled in the art. The source and detector are preferably placed on the side of the device that, following implantation, faces the chest wall, and are configured such that light cannot pass directly from the source to the detector. The placement on the side of the device that faces the chest wall maximizes the signal to noise ratio by 1) directing the signal toward the highly vascularized musculature and 2) shielding the source and detector from ambient light that enters the body through the skin.

The location of a microphone diaphragm 30, part of the preferred embodiment of the sound sensor, is indicated by the dotted line in FIGS. 2c and 3c. It is preferably placed such that it is directed toward the heart and lungs.

The embodiment of the sound sensor, which can be implemented using a microphone, accelerometer, or pressure transducer, is illustrated in FIG. 4. FIG. 4a shows a cross section of a portion of the monitor housing including microphone diaphragm 30 and illustrating the preferred embodiment of the diaphragm. In order to avoid the need for additional manufacturing steps, the diaphragm 30 is created during the same manufacturing step in which the device housing 36 is formed. This is achieved by including concentric ridges and grooves in the die such that the illustrated pattern results. The resulting ridges and groves in the formed device housing 36 produce a well-defined diaphragm 30 that vibrates according to the pressure wave of the incident sound, with greatest amplitude of oscillation at the diaphragm center. In addition to the ease of manufacturing that this embodiment offers, it is desirable because the preferred thickness of the diaphragm 30 is 0.005–0.015 inches, which is the typical wall thickness used in conventional implantable devices such as pacemakers and defibrillators. In an alternate manufacturing process, the ridges and grooves which define the diaphragm can be formed, coined, or machined in a separate step after the housing is formed or produced. Other arrangements of grooves and ridges are possible. In an alternate embodiment no groove is produced on the exterior of the housing. While this compromises the mechanical definition of the diaphragm, it provides a smooth exterior surface which minimizes the risk of infection.

A mechanical to electrical transducer 38, preferably a piezoelectric element such as that provided by MSI (Measurement Specialties, Inc, Sensor Products Division, Folsom, Calif.), is attached to the middle of diaphragm. A pair of leads 40 of the transducer 38 are connected to the inputs of a signal conditioning circuit (not shown), which is contained in the electronic circuit 12 shown in FIG. 1. The signal conditioning, filtering, and amplification appropriate for a piezoelectric sound transducer is well known in the field of sensors, and is therefore not presented here.

Figure 4A:
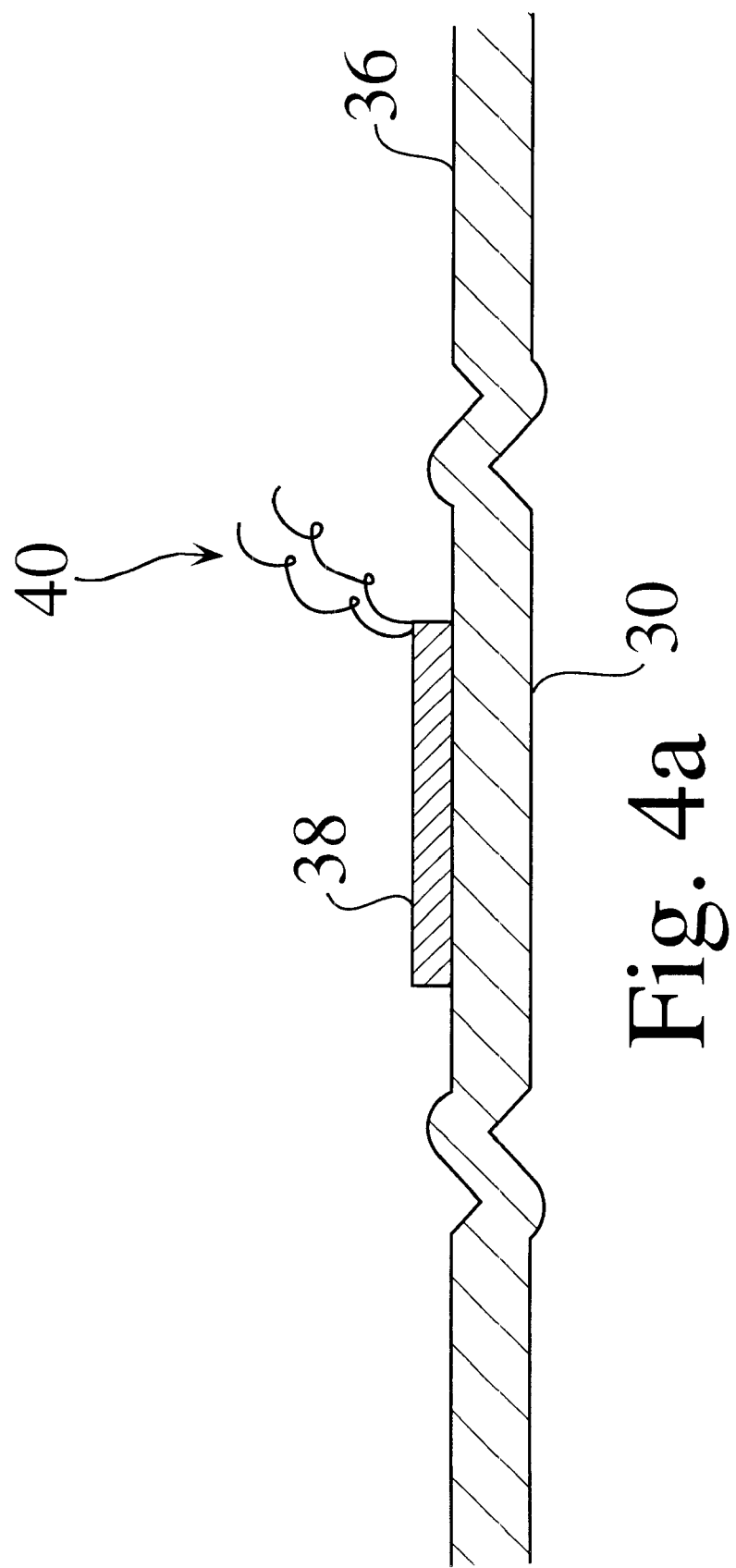
FIGS. 4a–4d show top sectional views of a sensor portion of the housing for various embodiments illustrating the microphone sensor.
Figure 4B:
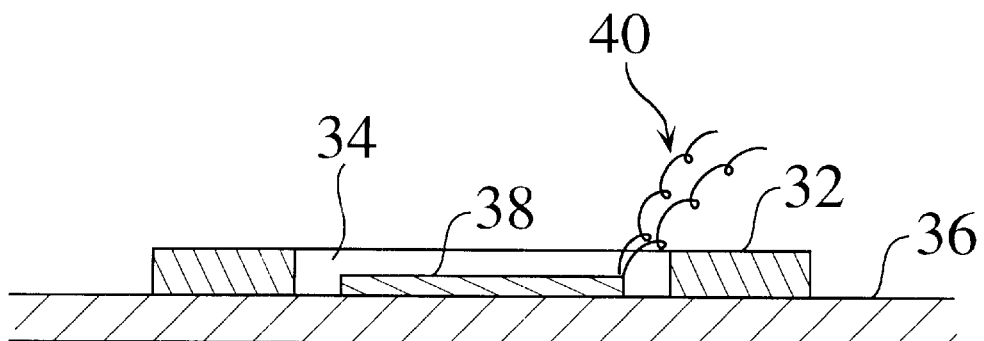

In an alternate embodiment illustrated in FIG. 4b, an annular disk or plate 32 with a circular hole 34 is attached to the inside of the monitor housing 36 using a laser weld, a resistance weld, glue, epoxy, or some other suitable attachment means. The annular disk or plate 32 can be a functional component of the monitor, such as a battery, capacitor, or circuit board. Because of the encircling rigid and relatively more massive annular disk or plate 32, the portion of monitor housing 36 that is exposed through the circular hole 34 is a mechanically well-defined diaphragm 30. When sound strikes the device housing 36, the diaphragm 30 moves according to the pressure wave of the sound, with the greatest movement amplitude occurring at the center of the diaphragm.

Figure 4C:
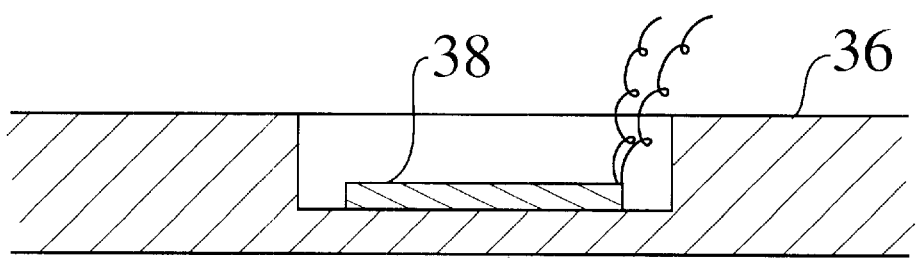

FIG. 4c shows an alternate embodiment of the sound sensor. Here the device housing 36 is formed, stamped, or machined such that the diaphragm thickness, typically 0.005 inches, is less than the thickness of the surrounding housing. This provides a mechanically well-defined diaphragm 30 which, when sound strikes the device, undergoes the largest amplitude deflection at its center. Transducer 38 is used to sense vibrational motion of diaphragm 30.

Figure 4D:
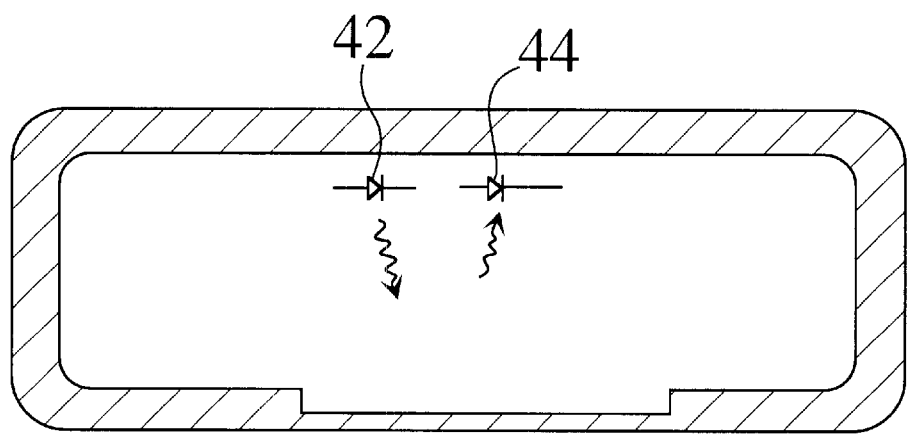

FIG. 4d shows an alternate embodiment of the mechanical-to-electrical transducer, in which a laser diode 42 and photodetector 44, such as a phototransistor, photodiode, piezoelectric, or thermoelectric material such as PVDF, are configured so that transduction is performed by laser interferometery. The technology of focusing elements and related circuitry, not shown, are well developed in the art of interferometery, as discussed in the book "Handbook of Modern Sensors," by Jacob Fraden.

Figure 5A:
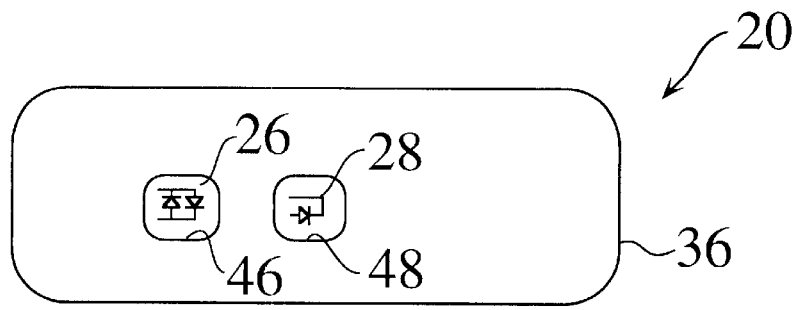
FIGS. 5a–5d show plan and sectional views illustrating the oxygen saturation and vascular plethysmography sensor.

FIG. 5a shows the preferred embodiment of the combined $O_2$ saturation and vascular plethysmography sensor of the monitor 20, in which the light source 26, preferably parallel and oppositely oriented red and infrared LEDs, are positioned such that light is directed into the overlying tissue, and the light detector 28, preferably a photodiode, is positioned such that it collects light reflected by the overlying tissue. The electronic circuitry associated with the light source and sensor is well known for external pulse oximeters, and is described in, e.g., U.S. Pat. Nos. 4,869,254 and 5,078,136, incorporated herein by reference. Tailoring the known art for an implantable, reflective embodiment is straightforward. In alternate embodiments, the plethysmography sensor or the $O_2$ saturation sensor, or both, might not be used in the monitor. Alternate embodiments of the plethysmography sensor use a single wavelength of light, or a broad spectrum of many wavelengths. In the alternate embodiments, the light source can be any source of radiant energy, including laser diode, heated filament, and ultrasound transducer. The detector can be any detector of radiant energy, including phototransistor, photodetector, ultrasound transducer, piezoelectric material, and thermoelectric material. In still other alternate embodiments vascular plethysmography is performed with non-radiant methods, including mechanical strain, electrical impedance, and pressure. Alternate embodiments of the $O_2$ saturation sensor might use more than two wavelengths. Alternatively, a single wavelength driven at two different current levels might be used, such as in the technique described by Cohen et al. in U.S. Pat. No. 4,815,469, which is incorporated herein by reference.

Figure 5B:
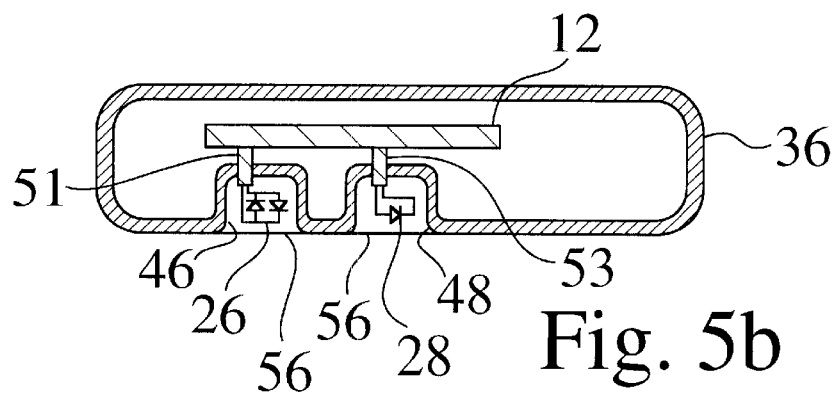
Figure 5C:
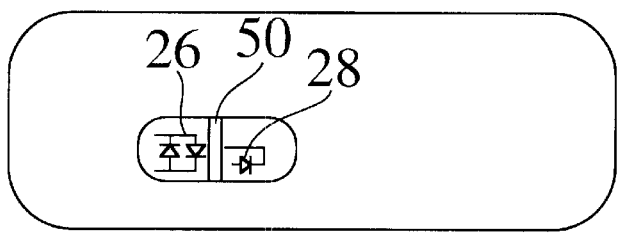
Figure 5D:
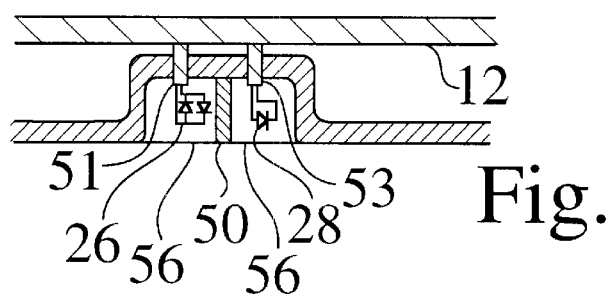

As with most of the sensors described here, the vascular plethysmography and arterial $O_2$ saturation sensors can be used in noninvasive, external embodiments, in contrast to incorporation in an implantantable monitor. These optical sensors are particularly attractive candidates for an external embodiment, since electrical contact with the skin or direct contact with subcutaneous tissue is not necessary, in contrast to, for example, ECG leads and chemical sensors, respectively. Furthermore, the sensors can be made small and can conveniently attach to a peripheral portion of the body, such as finger, toe, or ear, in contrast to, for example, a surface microphone, which is optimally position over the heart or great vessels. Thus, patients are likely to tolerate regular use of these sensors for an extended period of time, such as during sleep each night. Particular embodiments include a finger cuff, a wristband, a configuration resembling a watch, and a configuration resembling a clip-on earring. The sensor could be tethered to a larger unit containing the bulk of the electronic circuitry. In this case, the monitor would be worn primarily when the patient is sleeping. Alternatively, the raw data from the sensors could be continuously telemetered to a larger processor, which might be worn on the patient's clothing or located in the patient's home. In this case, the monitor could be worn both during sleep and during activity. Nevertheless, despite the cost advantages of an external embodiment, such an approach necessarily requires patient cooperation. Because of the disadvantages associated with this, as described above in Discussion of the Prior Art, the preferred embodiment for these sensors is in an implanted, extravascular configuration. Returning to the preferred embodiment of the combined vascular plethysmography and $O_2$ saturation sensor shown in FIG. 5a, the source 26 and detector 28 are placed in separate wells, 46 and 48, respectively, that are created when the monitor housing 36 is machined, formed, or cast. In the preferred embodiment each well 46 and 48 is formed using the minimum volume necessary to contain its feed through connector and optical device. Locating the source and detector in separate wells ensures that no light passes directly between them. In the alternate embodiment shown in FIG. 5c and 5d, source 26 and detector 28 are placed in the same well with an opaque barrier 50 placed between them. Returning to the preferred embodiment of FIGS. 5a and 5b, the source and the detector are physically positioned within the wells 46 and 48, respectively, such that the amount of light received at the detector is maximized. In particular, they are angled toward each other such that the direction of greatest optical power and sensitivity are aligned. Furthermore, in the preferred embodiment the optical devices have inherent directionality to avoid the need for lenses or other focusing elements, though these are used in alternate embodiments. The remaining space in the well is filled with epoxy 56 such that the surface of the monitor 20 is smooth and flat, thereby minimizing the risk of tissue trauma and infection. The optical source 26 and detector 28 are connected via feedthrough connections 51, 52, respectively, to the electronic circuit 12, thus ensuring hermeticity. Placing the optical components 26 and 28 in wells 46 and 48 thus enhances optical isolation while maintaining hermeticity, in contrast to the prior art, which risked the integrity of the hermetic seal by using a transparent window, or sacrificed optical isolation and therefore performance of the sensor, by placing the optical components together in a header. Furthermore, the solution of the present invention is applicable to both devices with headers and those without.

Figure 6:
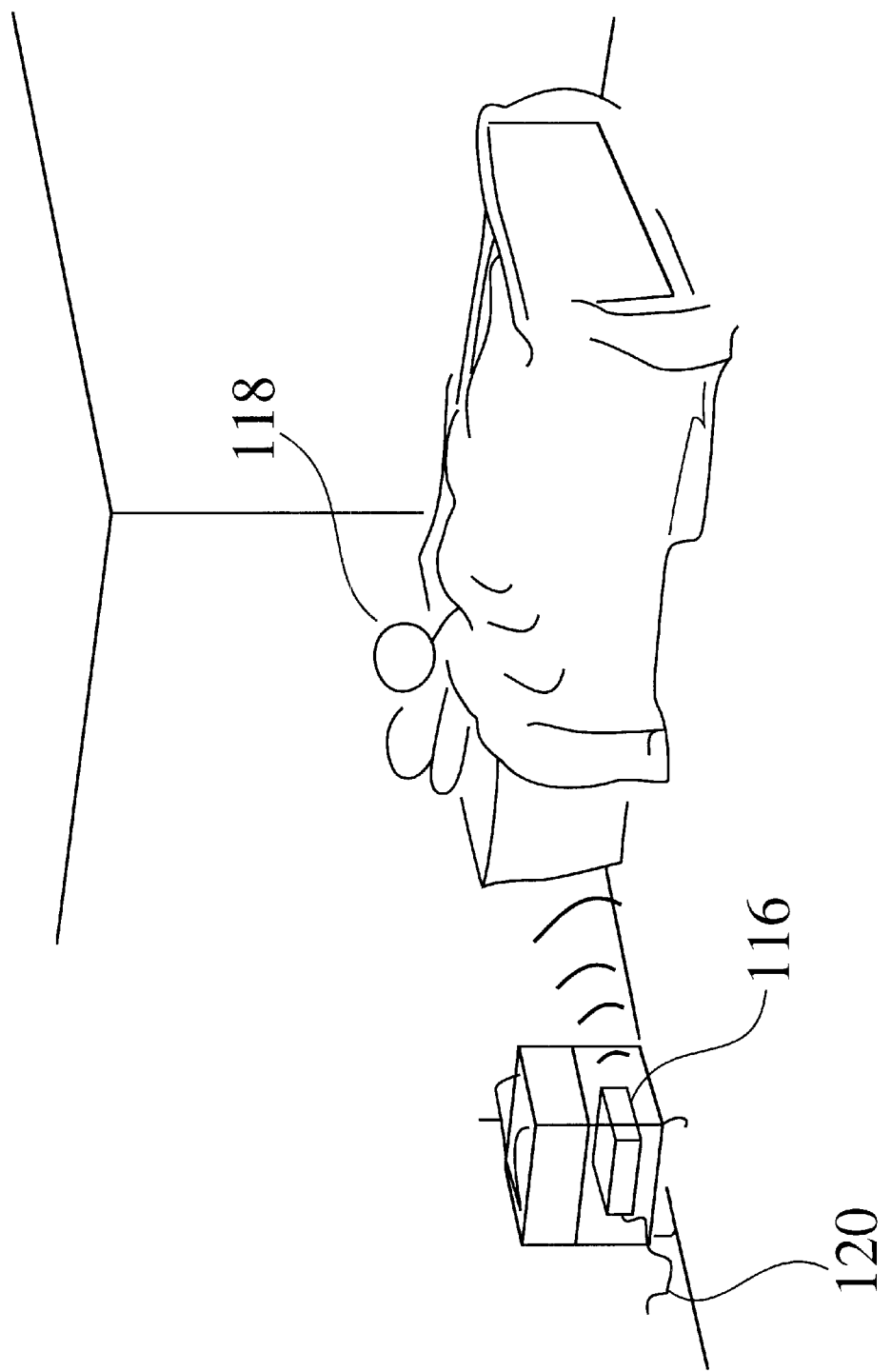
FIG. 6 illustrates the use of the telemetry-at-a-distance feature of the invention.

FIG. 6 illustrates the placement of the external telemetry unit 116 in the patient's bedroom, which, using telemetry at a distance, allows the transfer of data to and from the implanted device, without the active participation of the patient 118 or clinician. This is in contrast to the current art, which requires both the cooperation of the patient and the active participation of a health care provider. For example, in U.S. Pat. No. 5,342,408, incorporated herein by reference, a signal strength indicator is provided with allows the health care provider to optimally position the external telemetry antenna. In the preferred embodiment of the present invention, the external telemetry unit 116 is positioned in a location regularly frequented by the patient, such as the patient's bedroom, and is preferably connected to the telephone line 120, allowing transfer of data to a central location for further processing or review by a clinician.

Figures 7A, 7B:
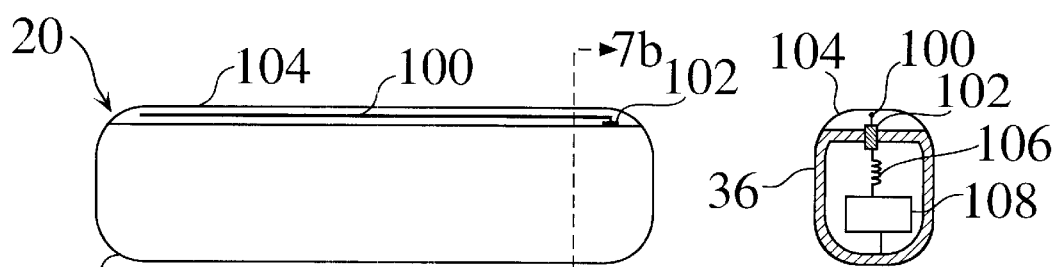
FIGS. 7a–7f provide various views of the preferred and alternate embodiments of the telemetry system of invention.

Telemetry is preferably implemented in the implantable monitor using the TR1000, a single-chip, low-power, 916.5 MHz transceiver manufactured by RF Monolithics, Dallas, Tex. The operating frequency of 916.5 MHz is preferred because of the modest requirements on antenna size it imposes; a standard ¼ wavelength whip antenna for this frequency is just 8 cm long. The implanted nature of the monitor, however, precludes the use of a simple whip antenna. Furthermore, omnidirectional antenna gain, an advantage not offered by the whip antenna, is desirable since the relative orientation of the implanted monitor and external telemetry unit is not know a priori and cannot be controlled, in contrast to the present state of the art, in which a clinician manually maneuvers the external antenna in order to optimize the signal strength. These considerations lead to the preferred embodiment of the antenna for the implantable monitor shown in FIG. 7a. The antenna 100 passes through the housing 36 of the monitor 20 via a feed-through connection 102, thus maintaining hermeticity. An insulating stabilizer 104 such as epoxy provides mechanical protection of the antenna 100 and electrically insulates it both from the overlying tissue and from the monitor housing 36, which acts as the antenna ground plane. This arrangement thus approximates the well-known stub antenna configuration. The antenna 100 is ideally 5 cm long. Referring now to FIG. 7b which is a cross-sectional view of monitor 20 along lines 7b–7b, a transceiver 108 is grounded to the monitor housing 36, thereby establishing the ground plane. An optional tuning inductor 106 is placed between the transceiver 108 and the antenna 100, which compensates for the impedance loading effects of tissue and internal components of the monitor (not shown). The inductor is preferably adjusted so that the impedance seen by transceiver 108 is 50 ohms.

Figure 7C:
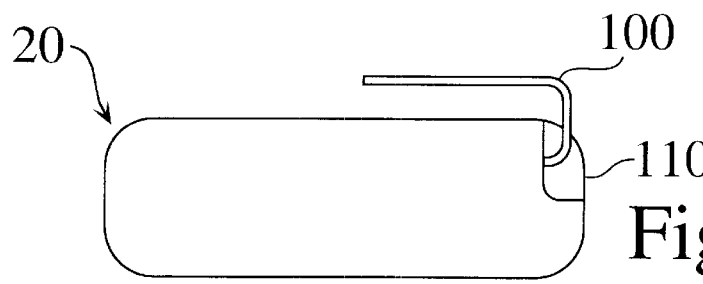

An alternate embodiment of the antenna is shown in FIG. 7c, where the antenna 100 is a flexible lead extending from a header 110 of the monitor 20. Alternatively, and in contrast to the header 110 which allows post-manufacturing attachment of the antenna 100, the base of the antenna 100 can be permanently secured with epoxy or other material to the monitor housing 36 during manufacture, a simpler and less expensive process than that required to form a functional header.

Figures 7D, 7E:
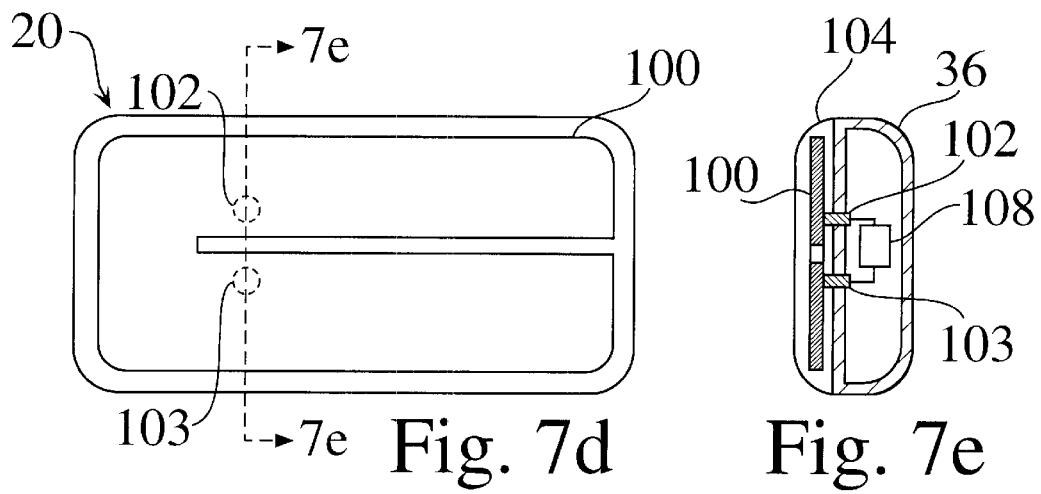

Yet another alternate embodiment of the antenna is shown in FIGS. 7d and cross-sectional view 7e, where the antenna 100 is implemented using the well-known slotted plane configuration. Dotted lines indicate the locations of the positive 102 and ground 103 feed-through connections of the transceiver 108. An insulator 104, preferably epoxy, mechanically stabilizes and electrically insulates the antenna 100 from the housing 36 of the monitor 20 and the overlying tissue.

Figure 7F:
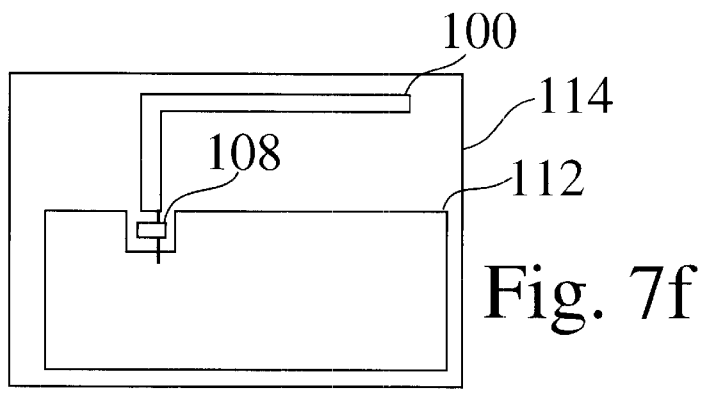

Still another alternate embodiment integrates the antenna 100 and ground plane 112 into the printed circuit board 114 used by the circuitry of the monitor, as shown in FIG. 7f. The antenna is thus placed entirely within the housing of the monitor. While internal placement of the antenna 100 will attenuate the signal transmitted from and received by the monitor, in some applications the reduced manufacturing costs may warrant this approach. The transceiver 108 is placed at the intersection of the antenna 100 and ground plane 112, and is connected to both.

In yet another embodiment the antenna is wrapped around the periphery of the monitor housing and insulated and secured in an epoxy encasement.

The implantable hemodynamic monitor is configured for subcutaneous or submuscular implantation. In the preferred embodiment, the routine operation of the monitor does not require patient participation or cooperation to monitor the patient's condition. The monitor automatically analyzes the data it acquires, recognizes a worsening of disease status, and notifies the patient of the need for physician consultation. As illustrated in FIG. 6, in the preferred embodiment an external telemetry unit 116 is available in the patient's home. When the implanted monitor recognizes worsening disease status, the patient is notified, and data is telemetered via the external telemetry unit 116 and via the telephone lines 120 to the physician or to a central location for further review.

In another embodiment the external home telemetry unit is not available. In this case when the patient is notified by way of an audible or vibrational warning signal from the monitor of potentially worsening disease status the patient should consult with a physician in person or over the telephone.

In yet another embodiment data is routinely and automatically conveyed to the external telemetry unit 116 which performs more computationally intensive analysis or delivers the data via telephone lines 120 to a central location for further analysis or review.

In still another embodiment, the patient may be required to actively participate in the routine telemetry of data to the external telemetry unit 116 or a central location, but would preferably not be required to actively participate in the data acquisition, thereby avoiding the disadvantages of noninvasive monitors as described above in Discussion of the Prior Art.

The electronic circuit shown in the functional block diagram of FIG. 1 provides the high level processing of the monitor. The preferred and alternative embodiments of the electronic circuit are now described. The implementation of the embodiments will be obvious to one skilled in the art, and will therefore not be presented in detail. The processing of data generated by the individual sensors will be described in detail below.

In the preferred embodiment, the electronic circuit does not acquire and process data continuously. Rather, the electronic circuit contains a timer that periodically initiates data acquisition. In the preferred embodiment, one of the sensors is an accelerometer. The output of the accelerometer is used by the electronic circuit to condition data acquisition on the activity of the patient. Specifically, data is scheduled to be acquired and processed at one-hour intervals. Data is acquired at the scheduled time if the patient has been at rest for a predetermined period, preferably at least 10 minutes. If the rest condition is not satisfied then data is acquired the next time the condition is satisfied.

There are a variety of levels of information that the electronic circuit can extract from the collection of sensors. For example, the electronic circuit may simply store raw data for later retrieval and analysis by a physician. In this embodiment, the device functions primarily as a tool that allows the physician to optimize medical therapy or work up a possible exacerbation. Alternatively, the raw data might be stored over an extended but relatively short period of time, such as 24 hours, and periodically and routinely conveyed by means of the transmitter to an external module which performs high level diagnostic analysis or data archiving. Yet another alternative is the preferred embodiment, in which the electronic circuit includes a microprocessor used to derive a high-level clinical diagnosis from the collection of sensor outputs. For example, the electronic circuit might deduce that an acute heart failure exacerbation is developing and that the patient and physician should be notified. In this case the device would activate the patient alert 14 shown in FIG. 1 to inform the patient that medical attention should be sought. In the preferred embodiment, the alert is provided through an electromechanical transducer that generates sound and mechanical vibration, which instructs the patient to telemeter data from the implanted hemodynamic monitor to the physician or emergency room. The physician can then review the data, interview the patient, and determine what course of action is appropriate. In the preferred embodiment, the electronic circuit assesses whether an exacerbation is developing by comparing the contents of an alert counter to a predetermined threshold, programmed by the physician or manufacturer. The alert counter is incremented for each measure calculated by the electronic circuit that suggests an exacerbation is developing. In the preferred embodiment, each measure is equally weighted, but in other embodiments more sensitive and specific measures may be weighted more heavily than less sensitive and specific measures.

Turning now to the preferred and alternate embodiments of specific sensors and the processing of their respective outputs by the electronic circuit, the general observation is made that the electronic circuit can provide processing at a variety of levels, depending on the sensor involved and the embodiment of the electronic circuit. Consider the case in which the sensor is an ECG electrode pair. The electronic circuit may simply sample the sensor output and digitally store the waveform for later review by a physician. In this way the physician can examine the raw data for the development of ST segment depressions or other morphology abnormalities, which are well known to clinicians, that suggest acute heart failure or ischemia. Alternatively, the device may itself analyze the data for the development of morphology abnormalities that suggest acute heart failure or ischemia. In another embodiment, the circuit may extract and store higher level information, such as the RR interval. In this way morphology information is lost but beat-to-beat rate information is retained. A further alternative is that the circuit may analyze the beat-to-beat rate information to extract a measure of sympathetic/parasympathetic balance, such as the ratio of low frequency to high frequency variability, a measure that is well known in the art. See, for example, the book "Heart Rate Variability," by Malik, M., and Camm, A. J., Eds, Futura Publishing Company, Inc, 1995, the disclosure of which is incorporated herein by reference. Thus, there is a hierarchy of abstraction that the electronic circuit might perform on the output of each sensor.

Two ECG electrodes 22 are used in the preferred embodiment, one at each end of the housing 36 of the monitor 20, as illustrated in FIG. 2. An ECG signal is derived from these two electrodes, in a way well-known to those skilled in the art. See, for example, "Medical Instrumentation," by J. G. Webster, John Wiley and Sons, Inc, 1998.

Figure 8:
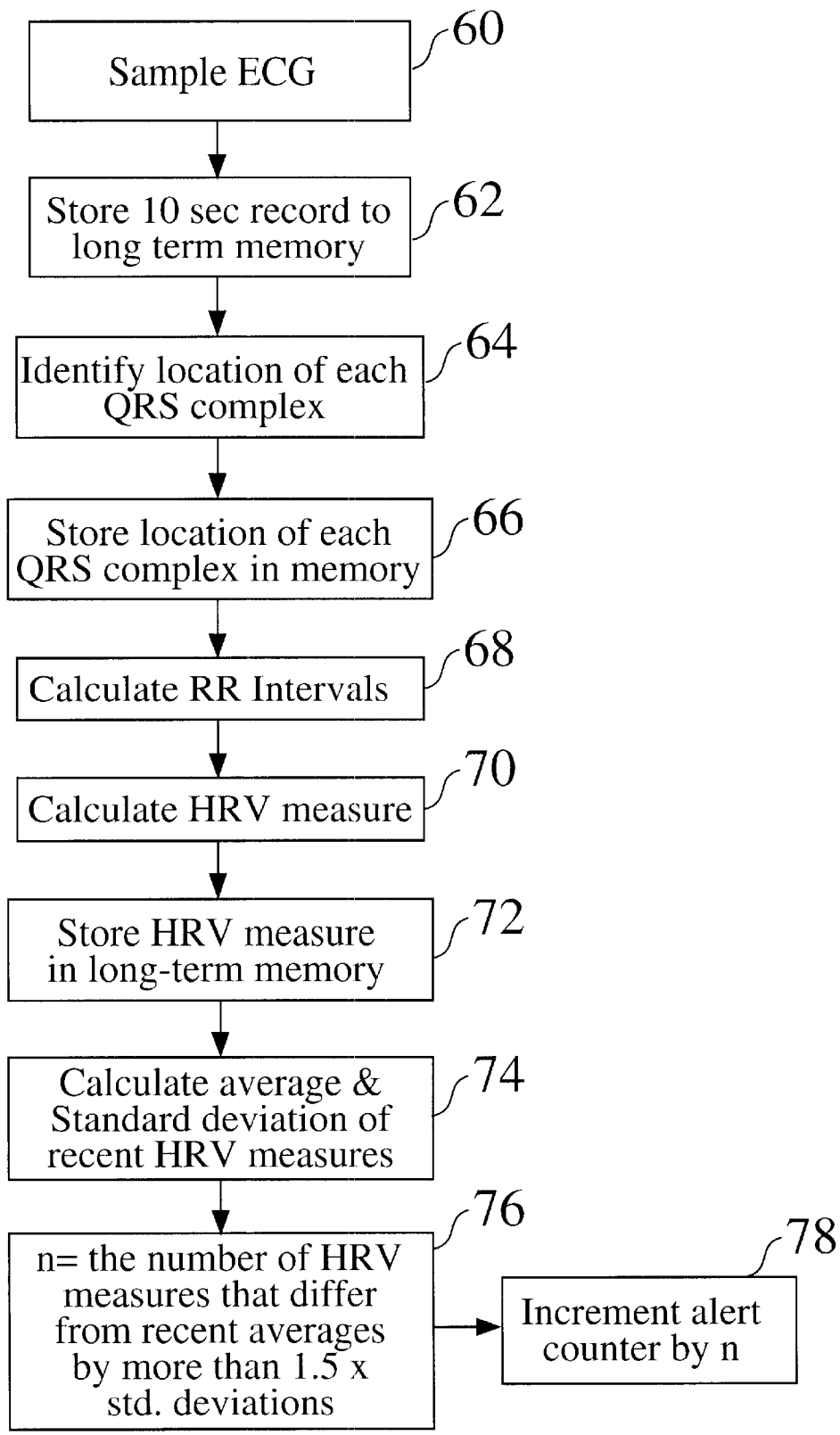
FIG. 8 is a flowchart which describes the processing performed by the electronic circuit on the output of the ECG sensors.

In the preferred embodiment the electronic circuit 12 shown in FIG. 1 processes the output of the ECG electrodes as illustrated in the flow chart of FIG. 8. First, in step 60, the ECG data is continuously sampled, preferably at 500 Hz for 5 minutes. Then, a short segment of the raw data, preferably 10 seconds in length, is stored at step 62 in long-term storage for later retrieval, thus allowing the physician to review the morphology for signs of ischemia. Next, the location of each QRS complex is identified in step 64 and stored in step 66 in memory for later use in the analysis of other sensor outputs. The intervals between QRS complexes are derived at step 68. From this data series, measures of heart rate variability (HRV) are derived at step 70, preferably the standard deviation of RR intervals, and the ratio of low to high frequency power, using methods well known to those skilled in the art. (See above referenced book by Malik, M., and Camm, A. J., Eds., and references contained therein.) An increase in sympathetic tone reflected in the HRV measures is consistent with a developing heart failure exacerbation. These HRV measures are then stored at step 72 in long-term memory for later retrieval and review by a physician. The electronic circuit computes the average and standard deviations of recent HRV measures at step 74, preferably using those obtained over the last 24 hours. The number of current HRV measures that differ from their respective recent average by more than 1.5 times their respective standard deviations is counted at step 76, and this sum is added to the alert counter contained in the electronic circuit at step 78. HRV analysis ultimately requires the times of cardiac contractions. In the preferred embodiment these are obtained using the ECG electrodes 22 incorporated into the monitor housing 36, as shown in FIG. 2. Other embodiments of HRV analysis are based on nonelectrical modalities such as vascular plethysmography (described below), ultrasound, pressure transduction, and heart sounds.

Figure 9:
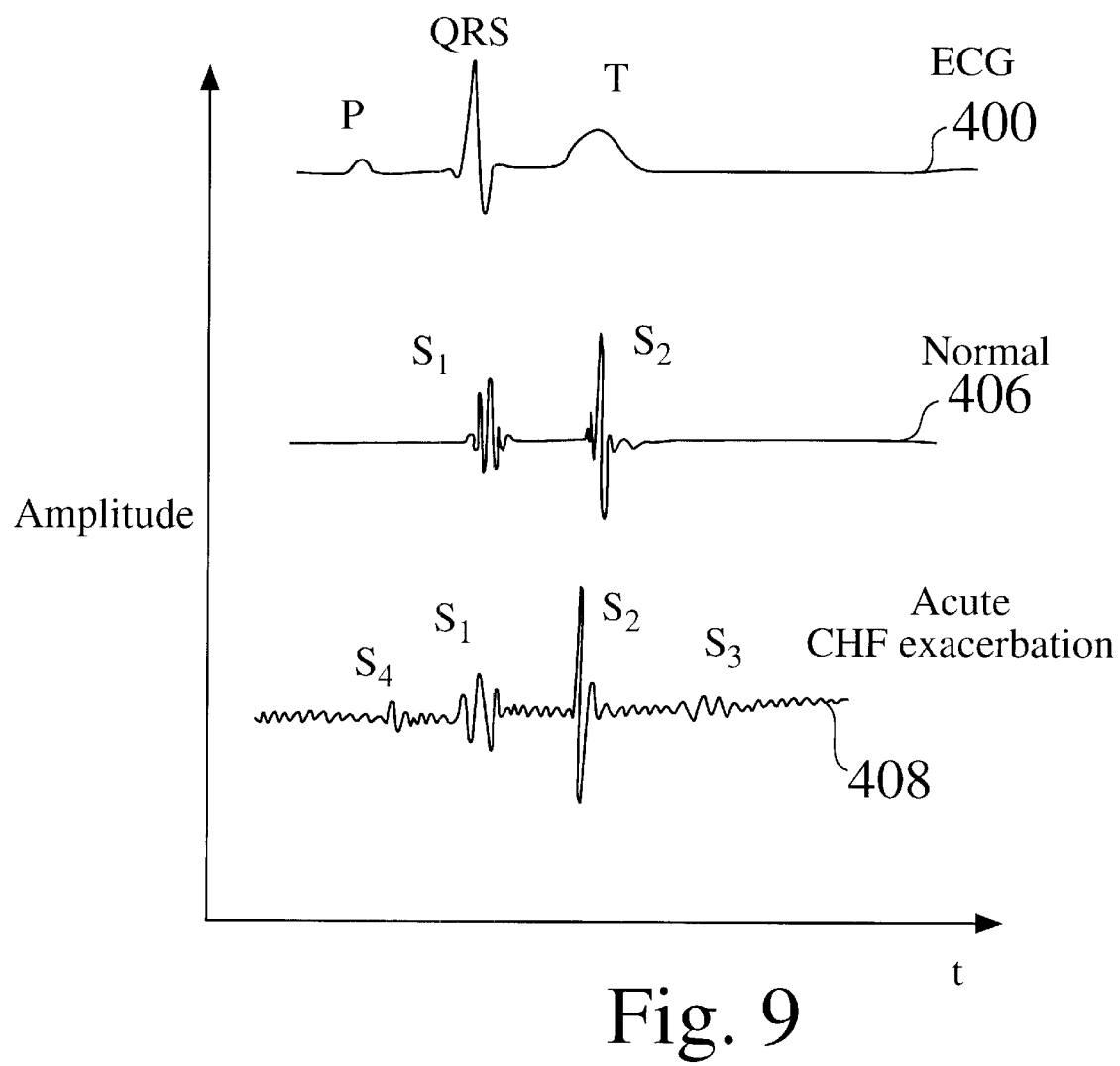
FIG. 9 illustrates a patient's ECG along with the phonocardiogram during a normal hemodynamic state and during an acute heart failure exacerbation.
Figure 10:
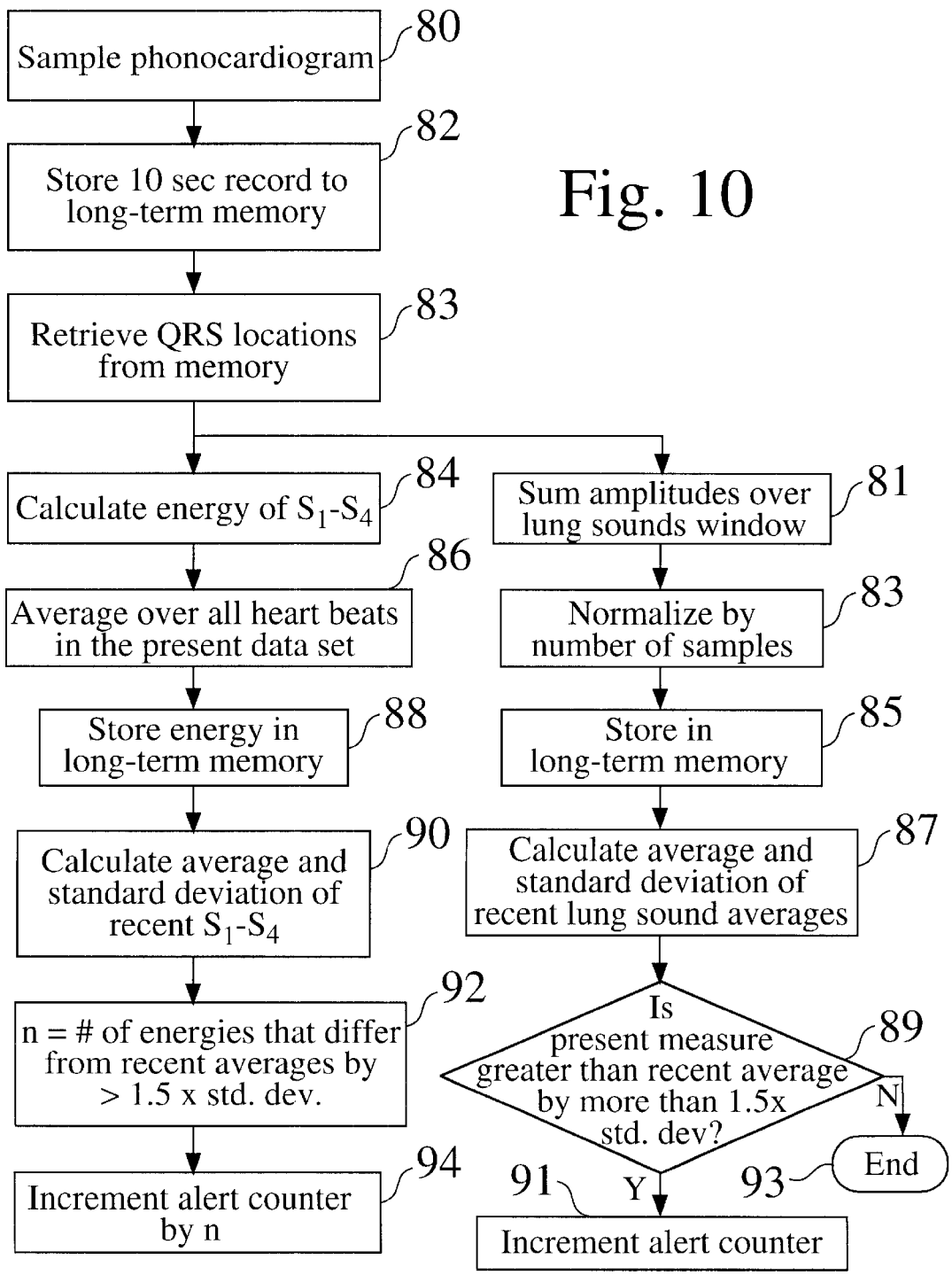
FIG. 10 is a flowchart which describes the processing performed by the electronic circuit on the output of the sound sensor.

FIG. 9 illustrates a phonocardiogram from the sound sensor with a patient in the normal state 406, and during a heart failure exacerbation 408. For timing reference the ECG 400 is also illustrated. As is well known to clinicians, extra heart sounds (S3, S4) or 'gallops,' develop during a heart failure exacerbation. Furthermore, the decreased cardiac contractility associated with an exacerbation decreases the force with which the tricuspid and mitral valves close, thereby decreasing the amplitude and energy of the S1 sound. In addition, the increased arterial blood pressure associated with an exacerbation increases the force with which the pulmonic and aortic valves close, thereby increasing the amplitude and energy of the S2 sound. Finally, the pulmonary rates, discussed below, of an acute heart failure exacerbation adds low amplitude, high frequency noise to the phonocardiogram. These changes can be seen in FIG. 9 by comparing the normal phonocardiogram 406 to that representing an acute heart failure exacerbation 408. In the preferred embodiment the electronic circuit 12 shown in FIG. 1 processes the output of the sound sensor as illustrated in the flow chart of FIG. 10. First, in step 80 the phonocardiogram data is sampled continuously and simultaneously with the ECG signal, preferably at 1 kHz for 5 minutes. Then in step 82 a short segment of the raw data, preferably 10 seconds in length, is stored in long-term storage for later retrieval, thus allowing the physician to review the morphology of the phonocardiogram for signs of an acute heart failure exacerbation. Next, at step 83 the location of each QRS complex is retrieved from memory, having been stored by the electronic circuit when the electronic circuit analyzed the output of the ECG sensor. Next, the energy of the four heart sounds is determined at step 84 by integrating the square of the phonocardiogram signal over windows located relative to the QRS complex. Taking t=0 to be the location of a given QRS complex, in the preferred embodiment S1 is determined by integrating over the window 0<=t <=50 msec, S2 is determined by integrating over the window 50<=t <=150 msec, S3 is determined by integrating over the window 150<=t <=250 msec, S4 is determined by integrating over the window –200<=t <=0 msec. These windows may be further optimized using average clinical data or data from a specific patient. In another embodiment the window sizes and locations might be made functions of the RR interval. In still other embodiments, function fitting to the time series, rather than integration, might be performed. For example, the functions $$f_i(t) = \frac{a}{\sqrt{2\pi\sigma^2}} \exp(-(t-b)^2/2\sigma^2)$$

might be fit to the square of the phonocardiogram signal, where a provides a measure of the total energy of the heart sound, b identifies the location of the sound in time, σ provides a measure of the sound's duration, and i indicates with which sound $S_i$ the particular function $f_i$ is associated. Still other embodiments might examine heart sound maximum amplitude, average amplitude, integrated amplitude, or duration.

Returning to the preferred embodiment, the heart sound energy measures are respectively averaged at step 86 over all the beats from the present data set, yielding averages for S1–S4. These four values are stored in long-term memory for later retrieval and review by a physician at step 88. The electronic circuit then computes the average and standard deviations of recent heart sound energy values at step 90, preferably using those obtained over the last 24 hours. The number of current heart sound measures that differ from their respective recent average by more than 1.5 times their respective standard deviations is counted at step 92, and this sum is added to the alert counter contained in the electronic circuit at step 94.

Pulmonary rates, which are high-pitched crackles associated with the pulmonary edema of an acute heart failure exacerbation, can be recognized from the sound sensor in a variety of ways. In the preferred embodiment, lung sounds are examined using the portion of the phonocardiogram not covered by the heart sound windows described above, i.e., the interval extending from 250 msec after one QRS complex to 200 msec before the next QRS complex. The average amplitude of the phonocardiogram is calculated by summing the magnitudes of all the samples in all the lung sound windows of the phonocardiogram, step 81 of FIG. 10, and dividing by the total number of samples, step 83. The number of samples is preferably a power of two, so that, as is obvious to one skilled in the art, division is implemented by a right shift. This measure of pulmonary rales is then stored in long-term memory at step 85 for later retrieval and review by a physician. In addition, the electronic circuit computes the average and standard deviations of pulmonary rates measures at step 87, preferably using those obtained over the last 24 hours. If the present pulmonary rales measure differs from the recent average by more than 1.5 times the standard deviations as determined at step 89, then the alert counter contained in the electronic circuit is incremented at step 91, otherwise, computation terminates with step 93.

Other embodiments of the pulmonary rales measure are possible. For example, in one embodiment the analog output of the sound sensor is bandpass filtered, e.g., using a low frequency cutoff of 400 Hz and a high frequency cutoff of 500 Hz, thereby eliminating the heart sounds, which are located below 300 Hz, and providing antialiasing filtering. The signal is then sampled at 1 kHz, and the sum of the magnitudes of each sample is computed. Alternatively, the sum of the squares of each sample can be computed. In another embodiment a higher frequency range is examined, such as 500–3000 Hz. In yet another embodiment the degree of pulmonary rales is quantified by processing in the analog domain. In this embodiment, the output of the sound sensor is rectified and integrated with analog circuits, the design and construction of which are known to those skilled in the art. The integrated output thus serves as the quantitative measure of pulmonary rales.

In alternate embodiments, the presence of pulmonary edema is detected with more direct measures than lung sounds. Thoracic impedance and ultrasound are two specific alternate embodiments. In addition to the changes in respiratory pattern associated with the Cheyne-Stokes respiration of pulmonary edema, described below, which both of these signals can detect, pulmonary edema will cause changes in their baseline readings. Specifically, pulmonary edema will cause a decrease in the baseline thoracic impedance, and an increase in reflected ultrasound signal from the lung fields.

Figure 11:
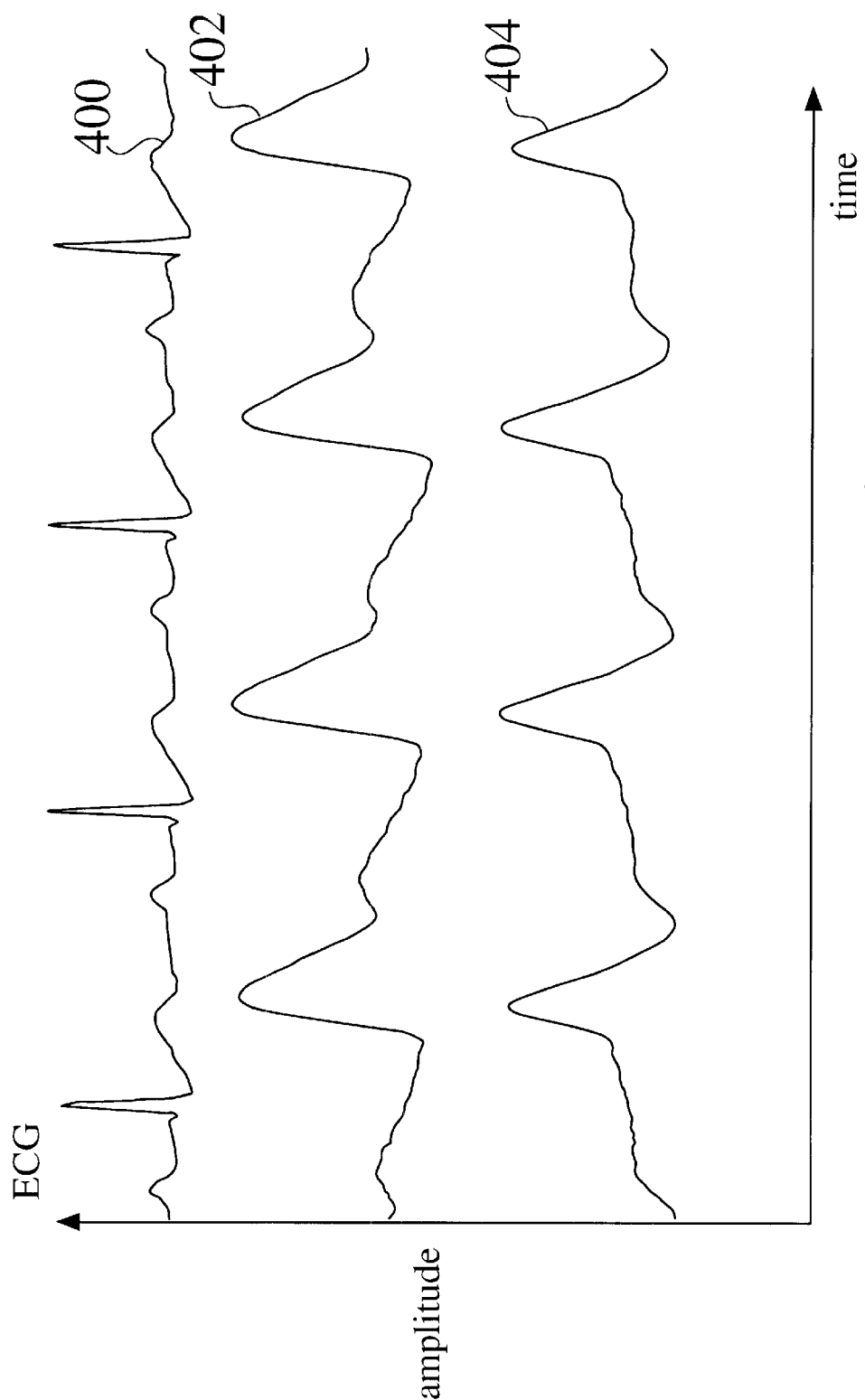
FIG. 11 illustrates the time tracing of the ECG and vascular plethysmograph.

The vascular plethysmograph is preferably obtained using a reflectance optical system, as described above in association with FIG. 5. A typical plethysmograph 402, 404, along with the ECG 400, is illustrated in FIG. 11. The signal 402 obtained using a wide band filter is shown in the middle trace, while the signal 404 obtained using a narrow band filter is shown at the bottom of the figure. To minimize sensitivity to motion, a narrow band filter centered at 15 Hz is preferable.

Figure 12:
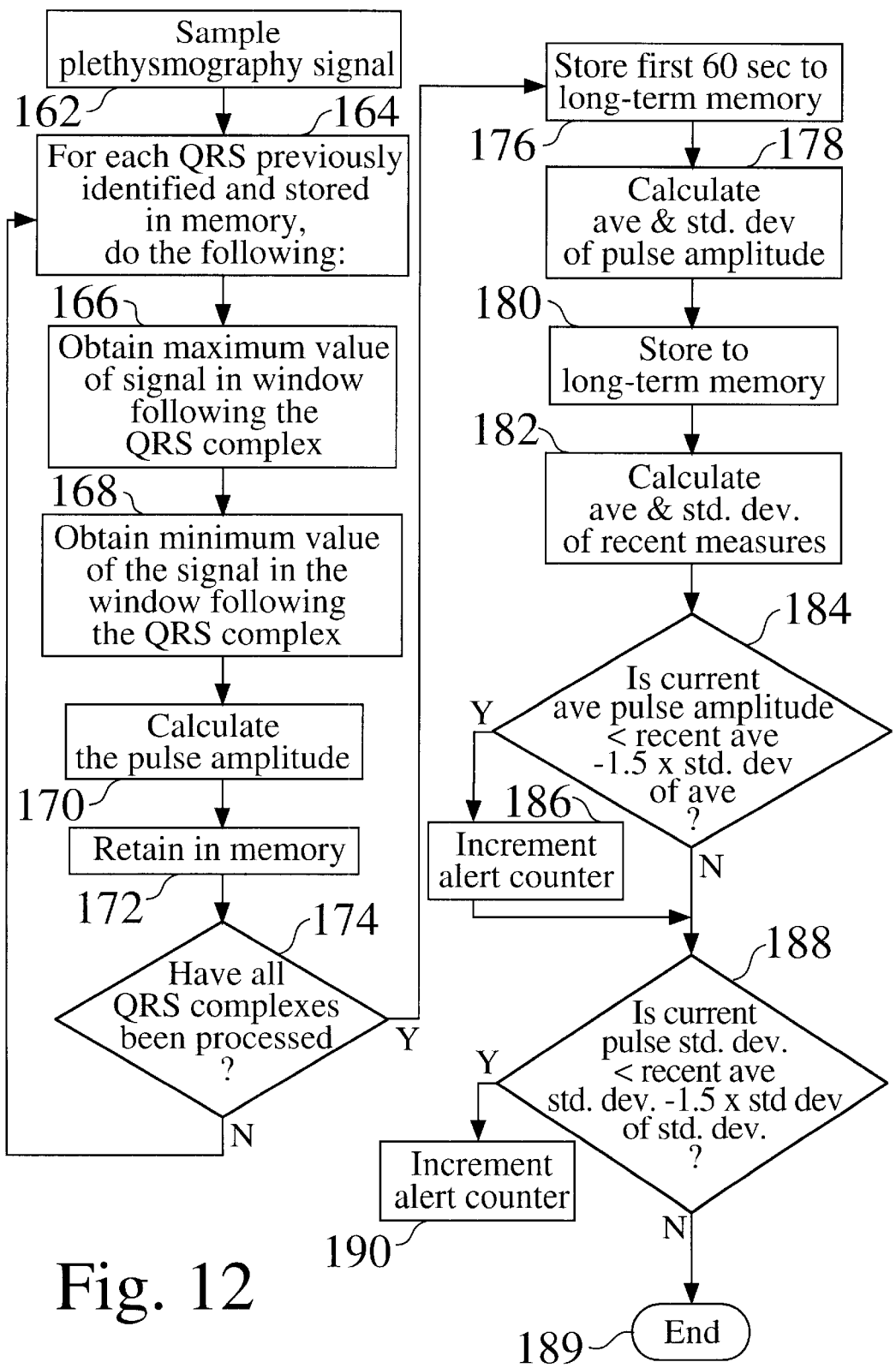
FIG. 12 is a flowchart which describes the processing performed by the electronic circuit on the output of the vascular plethysmography sensor.

The recorded data is processed as illustrated in FIG. 12. After narrow-band filtering, the plethysmograph is digitally sampled in step 162, preferably synchronously with the ECG previously described. In the preferred embodiment 5 minutes of data are acquired. Using the previously stored location of each QRS complex (step 66, FIG. 8) as a marker at step 164, the maximum and minimum values attained by the plethysmography signal in a window following the marker are obtained at steps 166 and 168, respectively. The window length is preferably 200 msec. The difference between the maximum and the minimum is a measure of the pulse amplitude for the given heart beat. It is calculated in step 170, and is retained in memory at step 172. When the end of the data is reached at step 174, a short segment of calculated pulse amplitudes, preferably 60 seconds in length, is stored in long-term storage at step 176 for later retrieval, thus allowing the physician to review the evolution of the pulse amplitude signal. In addition, the average and standard deviation of the pulse amplitude signal is calculated over the entire duration of the recording at step 178. These pulse amplitude measures are then stored in long-term memory for later retrieval and review by a physician at step 180. In addition, the data are analyzed as follows. In general terms, in the preferred embodiment both the pulse amplitude and the variability of the pulse amplitude are tested for a decrease in magnitude. The pulse amplitude is tested by calculating the average pulse amplitude from the current data set and comparing it to the average pulse amplitude calculated over the last 24 hours. The comparison is made relative to the standard deviation of the pulse amplitude calculated over the last 24 hours. Similarly, the variability of the pulse amplitude is tested by calculating the standard deviation of the pulse amplitude from the current data set and comparing it to the average standard deviation of the pulse amplitude calculated over the last 24 hours. The comparison is made relative to the standard deviation of the standard deviation of the pulse amplitude calculated over the last 24 hours. Specifically, the electronic circuit computes at step 182 the average and standard deviations of the recent pulse amplitude measures, preferably using those obtained over the last 24 hours. At step 184 the current pulse amplitude average is compared to the average of recently stored values. If it is less than the average by more than 1.5 times the standard deviation of the recent averages, then the alert counter contained in the electronic circuit is incremented at step 186. Similarly, if the current standard deviation is less than the average of recently stored standard deviations by more than 1.5 times the standard deviation of the recent standard deviations, step 188, then the alert counter contained in the electronic circuit is incremented at step 190. Otherwise, the algorithm terminates at step 189.

Figure 13:
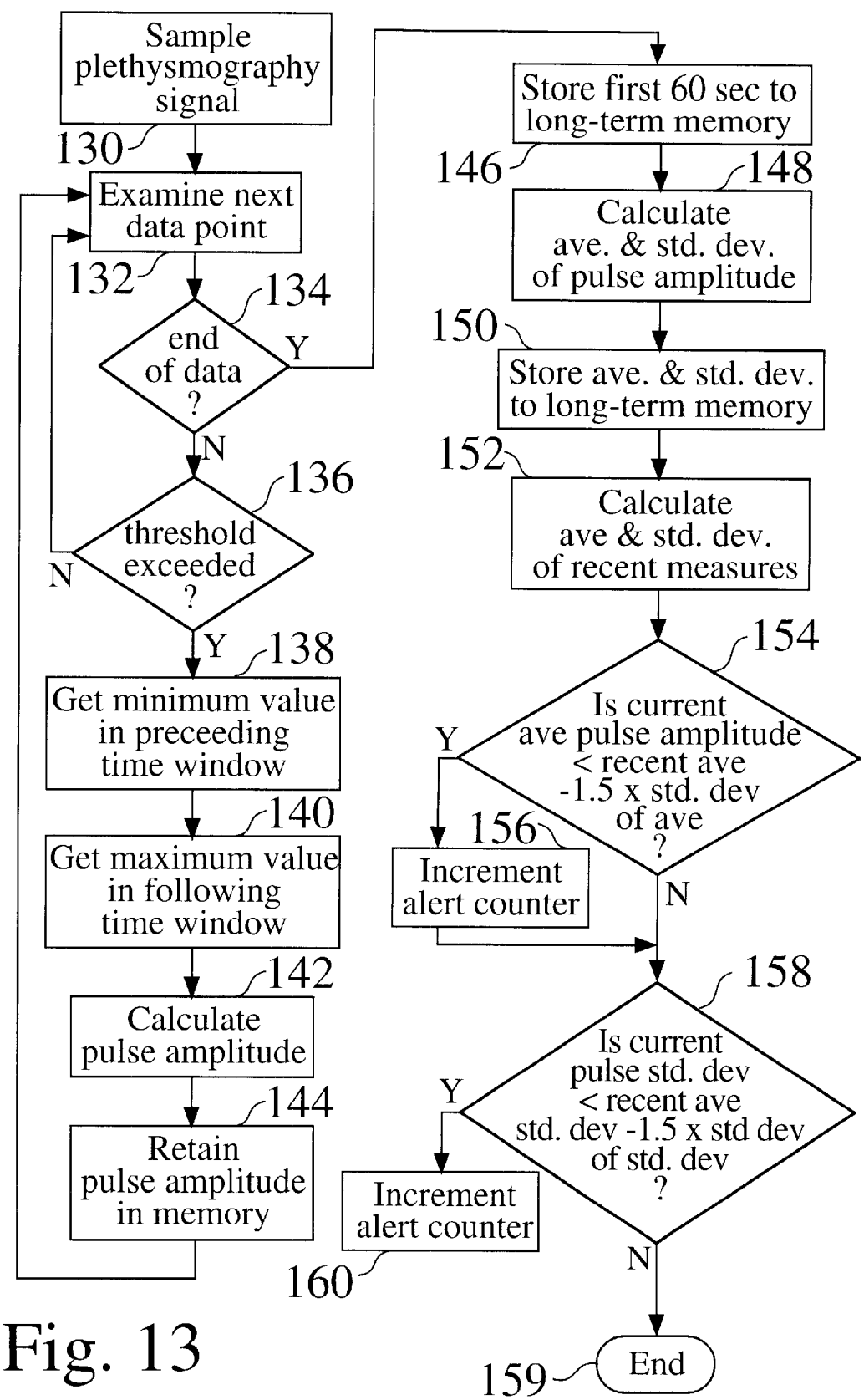
FIG. 13 is a flowchart which describes an alternate embodiment of the processing performed by the electronic circuit on the output of the vascular plethysmography sensor.

An alternate embodiment is possible in which the ECG signal is not used. Rather, as illustrated in FIG. 13, the plethysmography pulses are identified by threshold crossings. After narrow-band filtering, the plethysmograph is digitally sampled in step 130. Proceeding sample by sample through the data at step 132 until the end of the data is reached at step 134, crossings of a predetermined threshold are located at step 136. At each threshold crossing, the minimum value attained by the plethysmography in a preceding time window is located at step 138. Next, at step 140, the maximum valued achieved in a time window following the threshold crossing is located. Both windows are preferably 100 msec. The difference between the maximum and the minimum is a measure of the pulse amplitude for the given heart beat. The difference is calculated in step 142, and is retained in memory at step 144. Once the pulse amplitudes are obtained, i.e., the end of the data is reached at step 134, the remainder of the algorithm follows that of the preferred embodiment, described above in association with FIG. 12. Briefly, a short segment of calculated pulse amplitudes is stored in long-term storage at step 146, and the variability of the pulse amplitudes are characterized. Trends in both the amplitude (steps 148, 154) and the variability of the amplitude (steps 148, 158) are determined. Trends toward decreasing pulse amplitude or decreasing amplitude variability are interpreted as reflecting an increase in sympathetic tone, and the alert counter is incremented, steps 156 and 160, respectively.

An alternate embodiment examines the rate of change of vascular volume, rather than the amplitude of the volume change as described above. This signal can be derived in either the analog or digital domain, as is well known to those skilled in the art.

Figure 14:
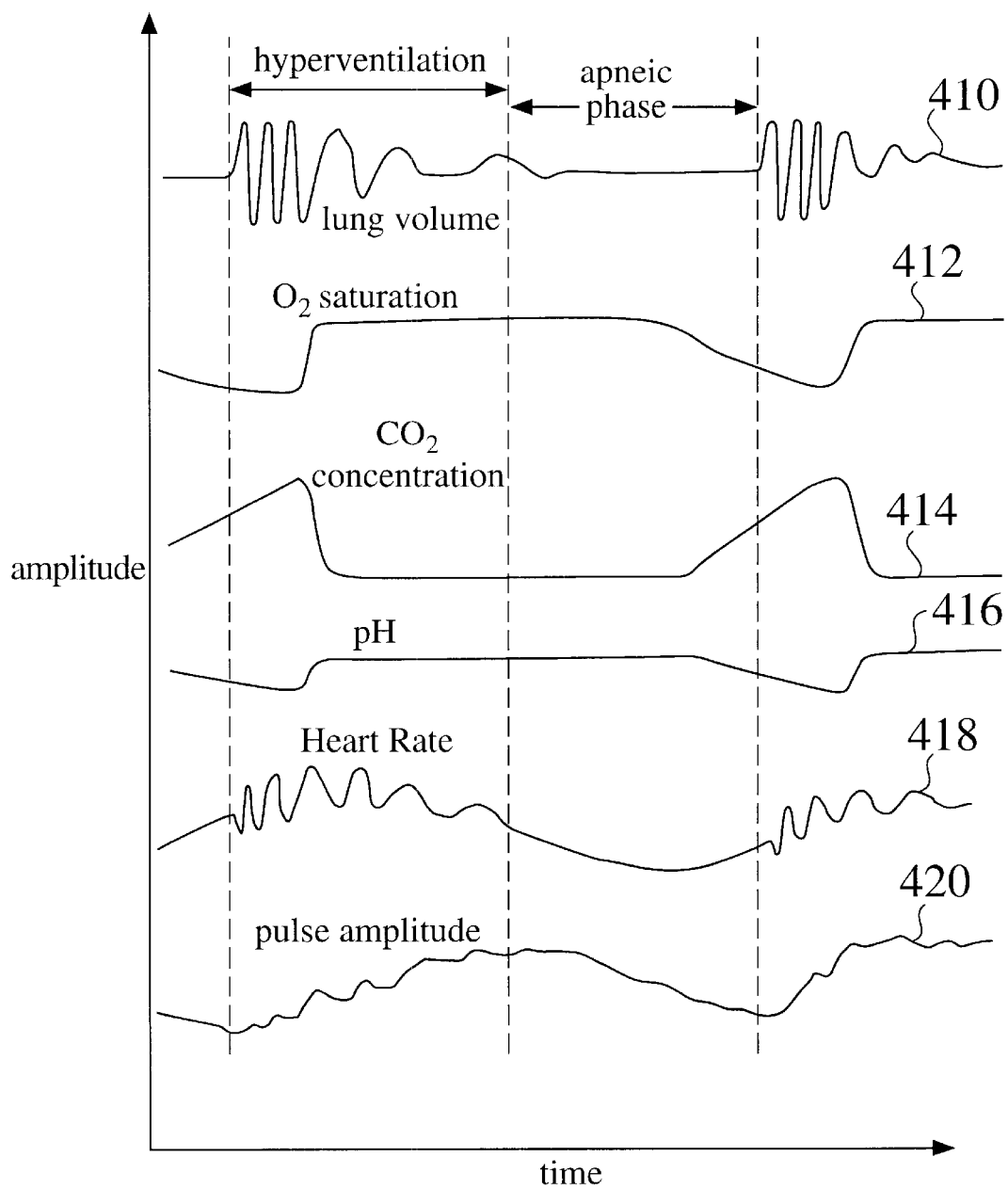
FIG. 14 illustrates the time tracing of the lung volume and various physiologic signals during Cheyne-Stokes respiration.

Another physiologic signal that is useful in assessing hemodynamic status is the respiratory pattern. A characteristic respiratory pattern, called Cheyne-Stokes respiration, is associated with the declining hemodynamic status of an acute heart failure exacerbation, and is thought to be an indirect result of developing pulmonary edema. As illustrated schematically in FIG. 14 with the tracing of lung volume 410 as a function of time, periods of apnea (absence of breathing) alternate with periods of hyperventilation. During the apnea period, blood $O_2$ saturation 412 falls and blood $CO_2$ content 414 increases. The increasing $CO_2$ levels result in a falling blood pH 416. Since the tissue is in equilibrium with the blood, the changes in chemical concentrations and pH that occur in the blood stream will result in changes in the tissue. Of particular interest is that the changes can be detected at the interface between the monitor housing and the tissue. During the apnea phase, as the blood $O_2$ level 412 falls, the autonomic nervous system enters an increasing sympathetic state induced by hypoxia. As illustrated in the figure, the heart rate 418 increases and, due to vasoconstriction induced by the sympathetic state, the pulse amplitude 420 falls, as assessed by vascular plethysmography. Subtle but significant modulation to the average heart rate 418 and pulse amplitude 420 are induced by respiration. During the apnea phase these modulations are absent. Their return marks the onset of the hyperventilation phase. Early in this phase the respiratory oscillations are rapid and of large amplitude. Later in the phase, in concert with the diminishing vigor and rate of respiration, the amplitude and frequency of the heart rate 418 and pulse amplitude 420 oscillations decrease. The Cheyne-Stokes respiratory pattern can thus be detected in a variety of general ways, including methods that directly assess the mechanical changes in the thorax associated with breathing, methods that indirectly assess these changes through their effects on heart rate and pulse amplitude, and methods that measure metabolic gases and chemicals and recognize the oscillatory changes that occur over time scales consistent with the Cheyne-Stokes respiratory pattern.

In the preferred embodiment, the monitor detects the presence of Cheyne-Stokes respiration using a number of methods. The mechanical changes associated with respiration are assessed using HRV derived from the ECG, the sympathetic/parasympathetic balance is assessed using vascular plethysmography, and the oxygen level of the body is measured using the extravascular blood $O_2$ saturation sensor and the electrochemical tissue $O_2$ sensor. Numerous other methods are possible. The mechanical changes associated with respiration can be detected using impedance plethysmography, a technique well known to those skilled in the art. Ultrasound can be used to determine thoracic diameter and thus estimate lung volume directly. In yet another alternate embodiment respiration is sensed using an pressure transducer placed within the pleural cavity and connected to the implantable hemodynamic monitor. Chemical sensors other than $O_2$ are used in alternate embodiments, such as $CO_2$, pH, and lactic acid.

Figure 15:
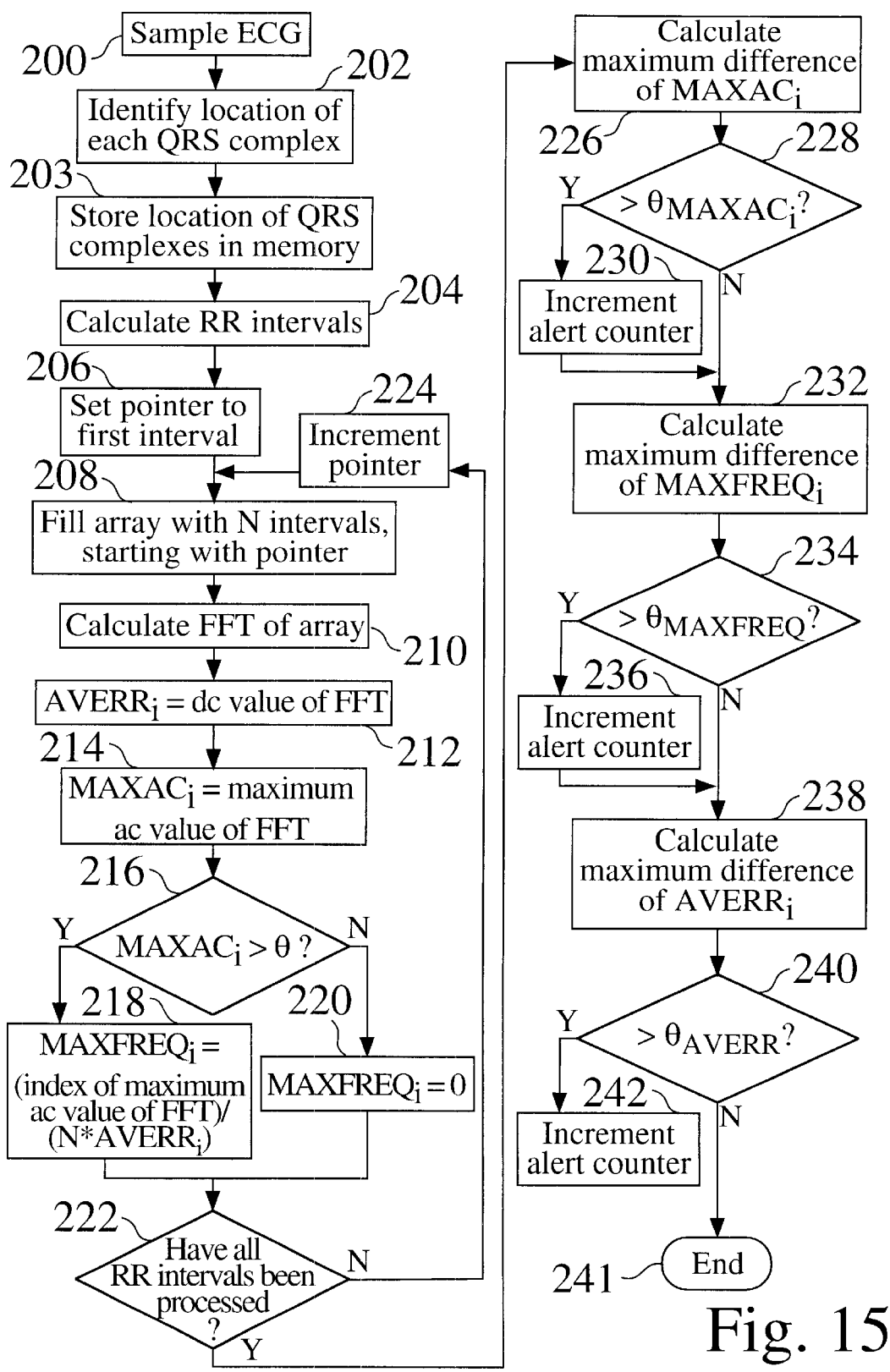
FIG. 15 is a flowchart which describes the processing performed by the electronic circuit on the output of the ECG sensor for the detection of Cheyne-Stokes respiration.

Consider first the preferred embodiment of the assessment of respiratory pattern for the detection of Cheyne-Stokes respiration. As shown in FIG. 15, HRV is used by first sampling the ECG at step 200. The location of each QRS complex is identified in step 202 and is stored in memory at step 203 for later use in the analysis of pulse amplitude, described below. The RR intervals are derived from the QRS complexes in step 204. A pointer is initialized to point to the first RR interval in the sequence at step 206. A temporary array is filled with a predetermined number N of RR intervals in step 208. In the preferred embodiment, N is set equal to 32, which allows subsequent analysis to recognize respiratory rates between 10 and 30 breaths per minute. At step 210, the Fast Fourier Transform (FFT) of the temporary array is obtained, preferably using a special purpose digital signal processing integrated circuit. At step 212, the average RR interval over the data in the temporary array is taken from the dc value of the FFT result and assigned to the variable $AVERR_i$. The maximum ac component of the FFT result is assigned to the variable $MAXAC_i$ at step 214. If this value is greater than a predetermined threshold $\theta$ then the variable $MAXFREQ_i$ is assigned the corresponding frequency as shown in step 218, otherwise, it is assigned the value zero, as shown in step 220. The test of whether all RR intervals have been processed in an FFT block is performed at step 222. If not, then the pointer is incremented at step 224, and control returns to step 208. If all RR intervals have been processed, then control continues at step 226, where all values of $MAXAC_i$ are examined to calculate the maximum difference in respiratory amplitude during the present analysis. If this difference is greater than a predetermined threshold $\theta_{MAXAC}$, tested at step 228, then the alert counter is incremented at step 236. Next, at step 232, the maximum difference in the respiratory frequency is calculated. If this difference is greater than a predetermined threshold $\theta_{MAXFREQ}$, tested at step 234, then the alert counter is incremented at step 236. Finally, at step 238, the maximum difference in the average RR interval is calculated. If this difference is greater than a predetermined threshold $\theta_{AVERR}$, tested at step 240, then the alert counter is incremented at step 242, otherwise, the algorithm terminates at step 241. As will be obvious to one skilled in the art, there are a variety of alternate possible embodiments of the analysis of HRV for the assessment of respiratory pattern.

Figure 16:
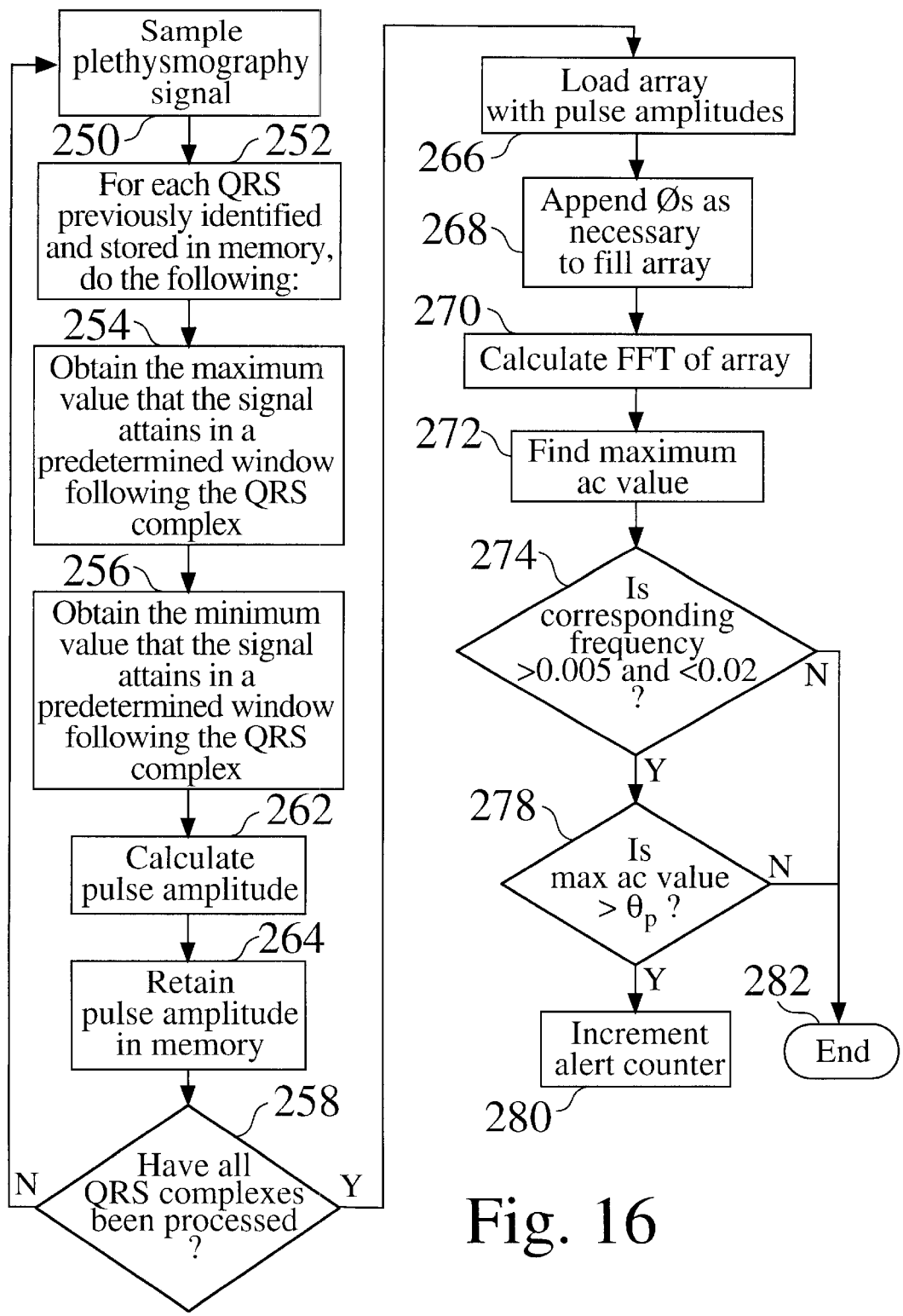
FIG. 16 is a flowchart which describes the processing performed by the electronic circuit on the output of the vascular plethysmography sensor for the detection of Cheyne-Stokes respiration.

Considering next the analysis of the sympathetic/parasympathetic balance assessed by vascular plethysmography, we note that in the context of Cheyne-Stokes respiration, oscillations in the sympathetic/parasympathetic balance that occur on the order of a few minutes are of interest. This is in contrast to longer-term and slower shifts in the sympathetic/parasympathetic balance, the analysis of which was described above in reference to FIGS. 8, 12, and 13. The analysis is presented in FIG. 16, where after narrow-band filtering, the plethysmograph is digitally sampled in step 250, preferably of 10 minutes duration and synchronously with the ECG previously described. Using the previously stored location of each QRS complex (step 203, FIG. 15) as a marker, the maximum and minimum values attained by the plethysmography signal in a window following the marker are obtained at steps 254 and 256, respectively. The window length is preferably 200 msec. The difference between the maximum and the minimum is a measure of the pulse amplitude for the given heart beat. It is calculated in step 262, and is retained in memory at step 264. When the end of the data is reached at step 258, the calculated pulse amplitudes are fetched from memory and loaded into an array, shown in step 266. Since the FFT algorithm requires $2^n$ data points, zeros are appended as necessary as shown in step 268, a process known as zero padding and well-known to those familiar with the art. Next, at step 270, the FFT is computed, preferably using a special-purpose digital signal processing integrated circuit. The results are analyzed in step 272 in order to identify the frequency component with the greatest amplitude. If, as tested in step 274, the frequency corresponding to this component lies between 0.005 and 0.02 Hz, the frequency range associated with Cheyne-Stokes respiration, and if, as tested in step 278, the amplitude of this maximum component exceeds a predetermined threshold, then the alert counter is incremented at step 280. As will be obvious to one skilled in the art, a variety of alternate embodiments of the analysis of respiratory pattern exist.

Figure 17:
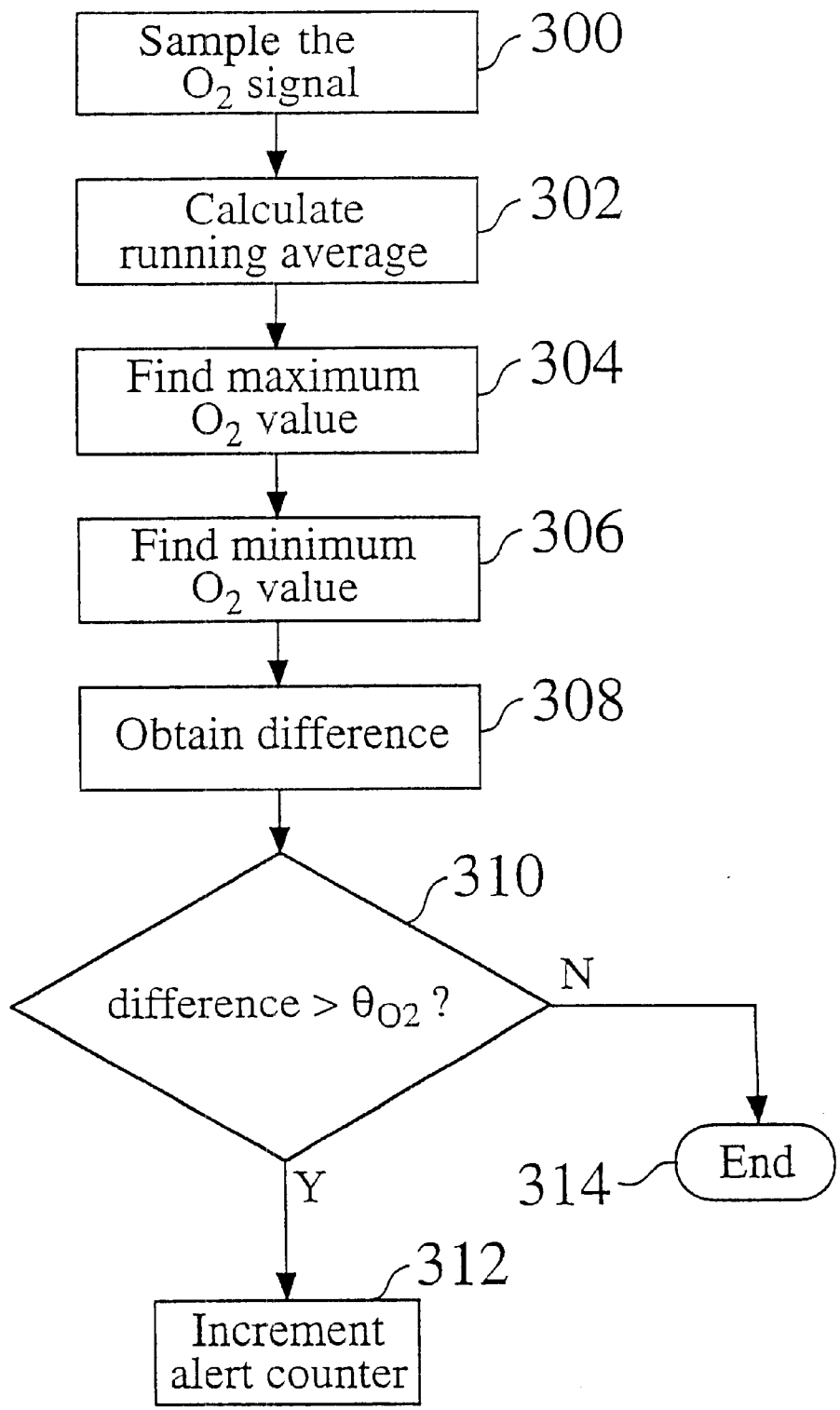
FIG. 17 is a flowchart which describes the processing performed by the electronic circuit on the output of the oxygen saturation and oxygen partial pressure sensors for the detection of Cheyne-Stokes respiration.

Finally, turning to the detection of Cheyne-Stokes respiration using the blood $O_2$ saturation sensor and the tissue electrochemical $O_2$ sensor, in the preferred embodiment both of these signals are analyzed according to the same algorithm. Consequently, the algorithm is described with reference to a generic $O_2$ sensor. As shown in FIG. 17, the $O_2$ signal is first digitally sampled in step 300 using the preferred sampling rate of 500 Hz. A running average is computed in step 302, thereby minimizing high frequency artifacts. The preferred window length for the running average is approximately 1 sec. Next, the maximum and minimum values attained by the $O_2$ signal are determined, as shown in steps 304 and 306, respectively. The difference between these is calculated, step 308, and if greater than the predetermined threshold $\theta_{O2}$, tested at step 310, the alert counter is incremented, step 312, otherwise, the algorithm terminates, step 314.

Figure 18:
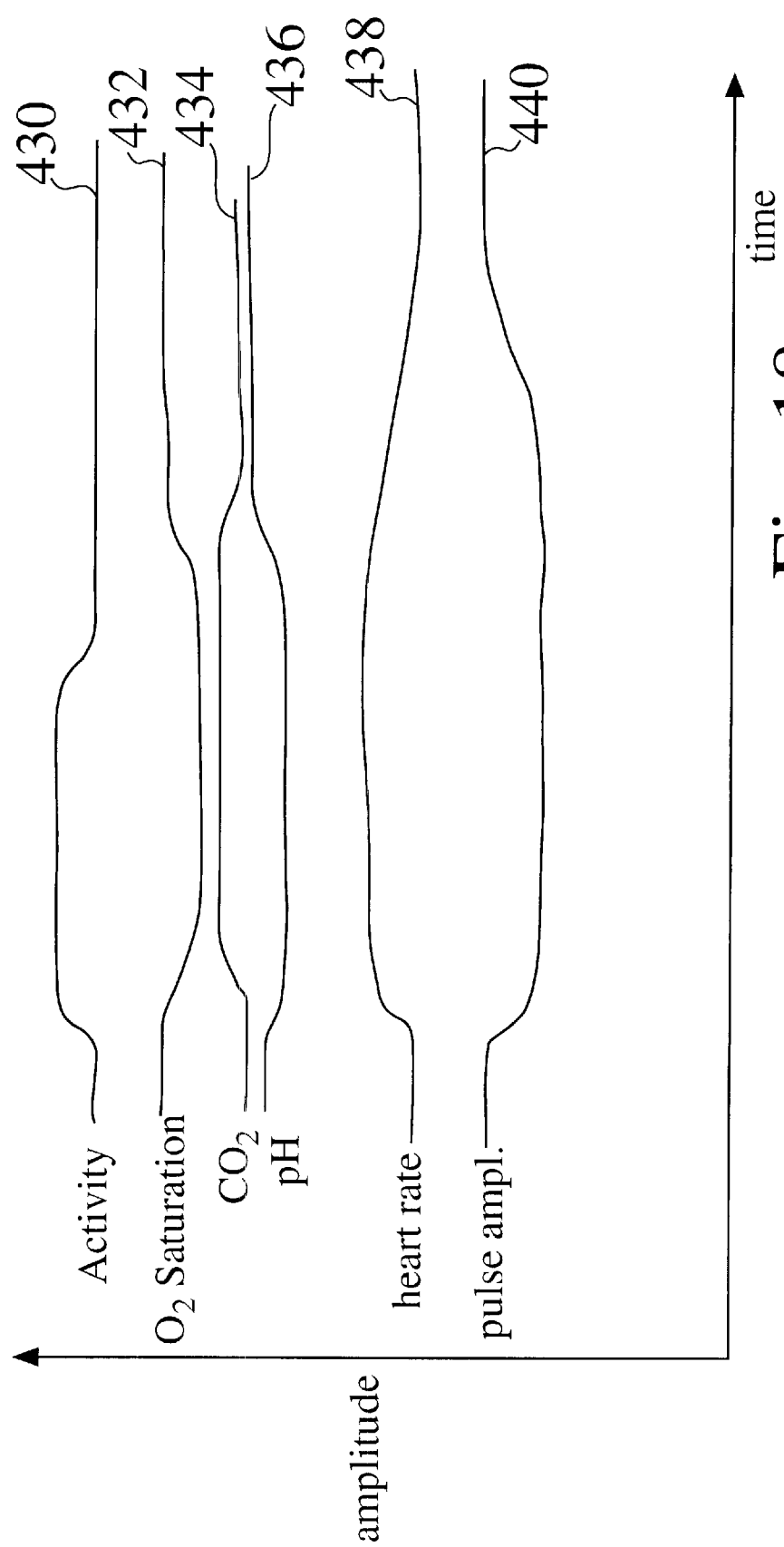
FIG. 18 illustrates the time tracing of various physiologic signals during activity-induced desaturation of hemoglobin.

In Cheyne-Stokes respiration, the saturation of hemoglobin with oxygen decreases because respiration ceases during the apnea phase. A different mechanism can also lead to the partial desaturation of hemoglobin. In this second mechanism desaturation is associated with activity. For a patient in acute heart failure, hemodynamic status is in a tenuous balance. The relatively minor increased demand of simple physical activity, such as walking across a room, can be enough to exceed the hemodynamic reserve. This process is exacerbated by the presence of pulmonary edema, which hinders the oxygenation of blood in the lungs. Thus, as illustrated in FIG. 18, an increase in physical activity 430 is associated with a decrease in $O_2$ saturation 432. As the $O_2$ level of the blood falls, the body resorts to anaerobic metabolism, which increases the level of lactic acid in the blood. The resulting acidemia is reflected in the falling pH 436, a process which is partially attenuated by the buffering action of the blood, in which free hydrogen combines with bicarbonate ion to yield $CO_2$ and water, thus increasing the $CO_2$ concentration 434 in the blood. At the same time, because of the increased sympathetic drive induced by hypoxia, the heart rate 438 increases and the pulse amplitude 440 decreases.

Figure 19:
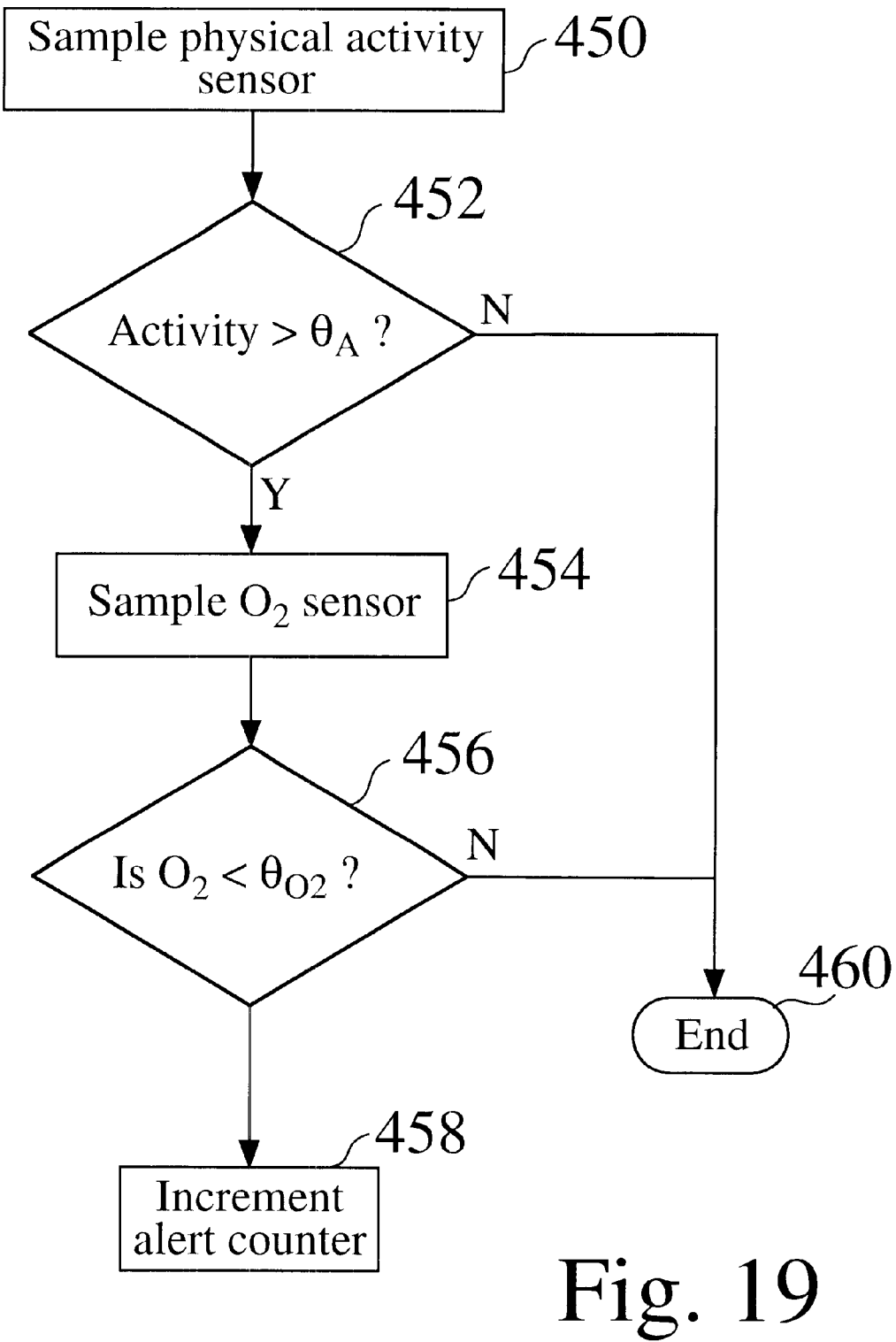
FIG. 19 is a flowchart which describes the algorithm used for detecting activity-related decrease in oxygen.

As suggested by FIG. 18, physical-activity-associated desaturation can be detected by monitoring a variety of physiological signals, including $CO_2$ concentration, pH, heart rate, and pulse amplitude. In the preferred embodiment, activity-related desaturation is detected by simultaneously monitoring the outputs of an activity sensor and the electrochemical $O_2$ sensor. The arterial hemoglobin saturation sensor is an alternative to the electrochemical $O_2$ sensor, but it has the disadvantage of being more sensitive to motion artifact. In contrast to the preferred embodiments of the analysis of the other sensors, which were conditioned on the patient being at rest, as described above, the present analysis is conditioned on the patient being active. As illustrated in FIG. 19, the output of a physical activity sensor is sampled at step 450 and compared to a predetermined threshold $\theta_A$ at step 452. If the threshold is not exceeded, the algorithm terminates 460. Otherwise, the output of the $O_2$ sensor is sampled 454 and compared to a predetermined threshold $\theta_{O2}$ at step 456. If $O_2$ level is below the threshold then the alert counter is incremented in step 458, otherwise, the algorithm is terminated at 460.

Figure 20:
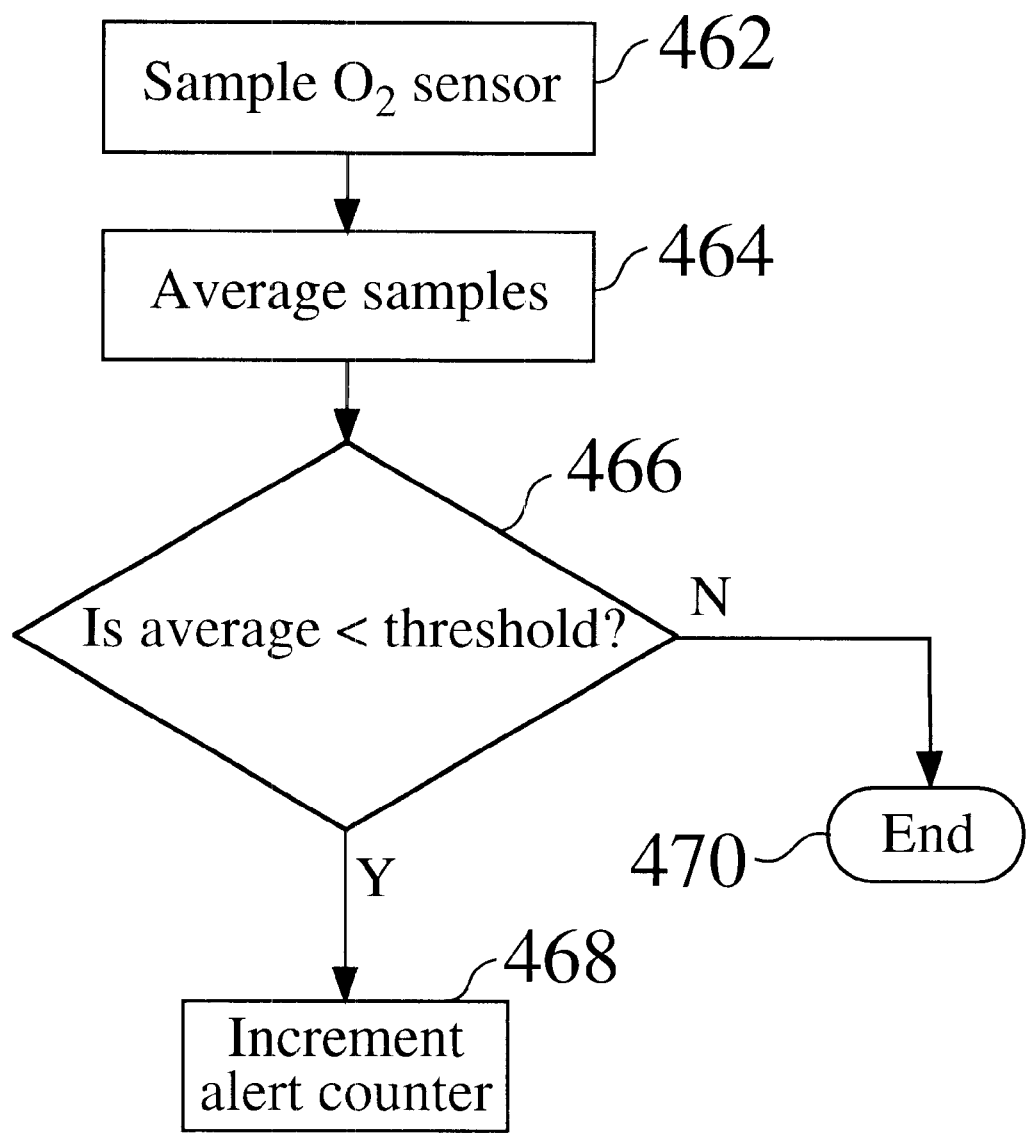
FIG. 20 is a flowchart which describes the algorithm used for the unconditioned detection of a decrease in oxygen.

Desaturation of hemoglobin is a nonspecific event. As described above in association with FIG. 14 it can be due to lack of respiration in the apnea phase of Cheyne-Stokes respiration, or as just described in association with FIG. 18 it can be due to increased physical activity and insufficient hemodynamic reserve. There are other causes for intermittent desaturation in addition to these. For example, the formation of a mucus plug in a pulmonary bronchiole or bronchus can lead to partial desaturation, a process which does not necessarily reflect the underlying hemodynamic status. In the preferred embodiment, the detection of Cheyne-Stokes-associated desaturation is conditioned on the patient being at rest, and the detection of activity-associated desaturation is conditioned on the patient being active. Conditioning the analysis in this way improves the specificity of the detection algorithm. In the preferred embodiment we perform one additional analysis of the $O_2$ sensor in which the analysis is not conditioned on other factors such as activity. Increments to the alert counter from this algorithm are thus less specific than from other sources, but because conditioning is not imposed they are more sensitive. In the preferred embodiment the oxygen sensor used by this algorithm is the electrochemical $O_2$ sensor. Other sensors such as the arterial $O_2$ saturation sensor can be used, but the electrochemical sensor is advantageous because it is less susceptible to motion artifact. The algorithm is presented in FIG. 20, where the output of the $O_2$ sensor is first sampled at step 462 then averaged, step 464. If the average is below a predetermined threshold at step 466 then the alert counter is incremented at step 468, otherwise, the algorithm is terminated at step 470.

What is claimed is:

1. An implantable medical device for monitoring the hemodynamic status of a patient comprising:

a lung sound sensor for extravascular implantation; and electronic circuitry coupled to said sensor for processing an output of said sensor and for providing an indication of hemodynamic status of said patient;

wherein said lung sound sensor and said electronic circuit detect pulmonary rales.

2. An implantable medical device for monitoring the hemodynamic status of a patient comprising:

a physiologic sensor for extravascular implantation, said sensor being capable of sensing a non-electrical parameter of said patient; and electronic circuitry coupled to said sensor for processing an output of said sensor and for providing an indication of hemodynamic status of said patient;

wherein said electronic circuitry is adapted to process the output of one or more sensors to provide an indication of the patient's physiologic state.

3. The device of claim 2 wherein said physiologic state is a predetermined phase of sleep.

4. The device of claim 2 wherein said physiologic state is the patient walking.

5. The device of claim 2, said electronic circuitry further including:
    a transmitter for telemetering data from said electronic circuitry to a receiver outside said patient's body;
    a memory for storing an output form said electronic circuitry for later analysis or telemetry by said transmitter; and
    wherein said electronic circuitry provides an output which is an indication of said patient's hemodynamic status.

6. The device of claim 5 wherein said electronic circuit stores in said memory the unprocessed output of said sensor, whereby said output can be later transmitted using said transmitter for analysis and interpretation outside said patient's body.

7. An implantable medical device for monitoring the hemodynamic status of a patient comprising:
    a physiologic sensor for extravascular implantation, said sensor being capable of sensing a non-electrical parameter of said patient; and
    electronic circuitry coupled to said sensor for processing an output of said sensor and for providing an indication of hemodynamic status of said patient;
    wherein said processing by said electronic circuitry quantifies the patient's sympathetic/parasympathetic balance, whereby hemodynamic status can be assessed.

8. The device of claim 7 further including a receiver connected to said electronic circuitry whereby instructions can be conveyed to said device from outside the body of said patient.

9. A method for chronically and acutely monitoring the medical status of a patient comprising:
    (a) providing an implantable, extravascular monitoring device having a physiologic sensor and electronic circuit for processing an output of said sensor; and
    (b) monitoring hemodynamic status using said sensor and said electronic circuit to monitor vascular volume.

10. An implantable hemodynamic monitor for monitoring the chronic hemodynamic status of a heart failure patient comprising:
    at least one extravascular physiologic sensor for sensing a hemodynamic parameter indicative of heart function;
    electronic circuitry coupled to an output of said physiologic sensor for chronically monitoring changes in the patient's hemodynamic status indicative of heart failure exacerbation; and
    means coupled to said electronic circuitry for warning the patient or a healthcare provider of an indicated exacerbation.

11. The monitor of claim 10 wherein said at least one extravascular physiologic sensor is selected from among a vascular plethysmography sensor, an arterial hemoglobin saturation sensor, a heart and lung sound sensor, a thoracic impedance plethysmography sensor and an electrocardiogram sensor.

12. The monitor of claim 10 and further including a telemetry circuit for telemetrically transmitting information to an external unit.

13. The monitor of claim 12 wherein said telemetry circuit periodically operates automatically to telemeter information to said external unit.

14. An implantable medical device for monitoring the hemodynamic status of a patient comprising:
    a physiologic sensor for extravascular implantation, said sensor being capable of sensing heart sounds of said patient;
    electronic circuitry coupled to said sensor for processing an output of said sensor including detecting cardiac gallops and changes in heart sound energy and for providing an indication of hemodynamic status of said patient.

15. An implantable medical device for monitoring the hemodynamic status of a patient comprising:
    a physiologic sensor for extravascular implantation, said sensor being capable of sensing a physiologic parameter indicative of vascular volume of said patient; and
    electronic circuitry coupled to said sensor for processing an output of said sensor and for providing an indication of hemodynamic status of said patient.

16. The device of claim 15 and further including an electrocardiogram (ECG) sensor wherein said electronic circuit calculates a measure of variability of cardiac electrical activity from an output of said ECG sensor.

17. The device of claim 15 and further including:
    a light source positioned to radiate light energy toward vascularized tissue of said patient's body; and
    a light detector positioned to detect light radiated by said light source and reflected from said tissue and provide an output signal to said electronic circuitry;
    wherein said electronic circuitry measures vascular volume by recording changes in detected light.

18. The device of claim 15 wherein said sensor comprises a mechanical transducer that detects changes in cardiac pulse amplitude.

19. An implantable medical device for monitoring the hemodynamic status of a patient comprising:
    a physiologic sensor for extravascular implantation for measuring metabolic chemicals within a patient's tissues; and
    electronic circuitry coupled to said sensor for processing an output of said sensor and for providing an indication of hemodynamic status of said patient.

20. The device of claim 19 wherein said sensor measures tissue pH.

21. The device of claim 19 wherein said sensor measures tissue $O_2$.

22. The device of claim 19 wherein said sensor measures tissue $CO_2$.

23. An implantable medical device for monitoring the hemodynamic status of a patient comprising:
    an intrathoracic pressure sensor for extravascular implantation; and
    electronic circuitry coupled to said sensor for processing an output of said sensor and for providing an indication of hemodynamic status of said patient.

24. A method for chronically and acutely monitoring the medical status of a patient comprising:
    (a) providing an implantable, extravascular monitoring device having a physiologic sensor and electronic circuit for processing an output of said sensor; and
    (b) monitoring hemodynamic status using said sensor and said electronic circuit to monitor metabolic chemicals within tissue of the patient.

25. A method for chronically and acutely monitoring the medical status of a patient comprising:
    (a) providing an implantable, extravascular monitoring device having a physiologic sensor and electronic circuit for processing an output of said sensor;

(b) monitoring hemodynarnic status using said sensor and said electronic circuit;

(c) determining with said electronic circuitry if the patient's hemodynamic status is progressively worsening; and (d) if the patient's hemodynamic status is progressively worsening the device providing a warning of said worsening status.

26. An implantable hemodynamic monitor for monitoring the chronic hemodynamic status of a heart failure patient comprising:

at least one extravascular physiologic sensor for sensing a hemodynamic parameter indicative of heart function;

electronic circuitry coupled to an output of said physiologic sensor for chronically monitoring changes in the patient's hemodynamic status indicative of heart failure exacerbation; and a telemetry circuit for telemetrically transmitting information to an external unit;

wherein said telemetry circuit periodically operates automatically to telemeter information to said external unit.

27. An implantable hemodynamic monitor for monitoring the chronic hemodynamic status of a heart failure patient comprising:

at least one physiologic sensor for sensing a hemodynamic parameter indicative of heart function;

electronic circuitry coupled to an output of said physiologic sensor for chronically monitoring changes in the patient's hemodynamic status indicative of heart failure exacerbation; and a telemetry circuit for telemetrically transmitting information to an external unit;

wherein said telemetry circuit periodically operates automatically to telemeter information to said external unit.

* * * * *